US009879267B2

(12) United States Patent
Lackner et al.

(10) Patent No.: US 9,879,267 B2
(45) Date of Patent: Jan. 30, 2018

(54) GENETIC VARIATIONS ASSOCIATED WITH DRUG RESISTANCE

(75) Inventors: Mark Lackner, South San Francisco, CA (US); Lukas C. Amler, Foster City, CA (US); Guy Cavet, Burlingame, CA (US); Carol O'Brien, Pacifica, CA (US); Ajay Pandita, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 282 days.

(21) Appl. No.: 12/922,420

(22) PCT Filed: Mar. 12, 2009

(86) PCT No.: PCT/US2009/036985
§ 371 (c)(1),
(2), (4) Date: Feb. 24, 2011

(87) PCT Pub. No.: WO2009/114711
PCT Pub. Date: Sep. 17, 2009

(65) Prior Publication Data
US 2011/0177099 A1 Jul. 21, 2011

Related U.S. Application Data

(60) Provisional application No. 61/036,874, filed on Mar. 14, 2008, provisional application No. 61/054,064, filed on May 16, 2008.

(51) Int. Cl.
*C12Q 1/68* (2006.01)
*C12N 15/113* (2010.01)
*A61K 47/48* (2006.01)

(52) U.S. Cl.
CPC .... *C12N 15/1138* (2013.01); *A61K 47/48407* (2013.01); *A61K 47/48584* (2013.01); *C12Q 1/6886* (2013.01); *C12N 2310/14* (2013.01); *C12Q 2600/106* (2013.01)

(58) Field of Classification Search
None
See application file for complete search history.

(56) References Cited

U.S. PATENT DOCUMENTS

| 2002/0001587 | A1 | 1/2002 | Erickson et al. |
| 2004/0101834 | A1 | 5/2004 | Assaraf et al. |
| 2006/0275305 | A1* | 12/2006 | Bryant ...................... 424/155.1 |
| 2007/0015913 | A1 | 1/2007 | Chen et al. |

FOREIGN PATENT DOCUMENTS

| WO | WO 2001/00244 | 1/2001 |
| WO | WO 2001/00245 | 1/2001 |
| WO | WO 2001/083496 | 11/2001 |
| WO | WO 2003/044215 | 5/2003 |
| WO | WO 2004/075842 | 9/2004 |
| WO | WO 2004/075842 A2 | 9/2004 |
| WO | 2005/058028 | 6/2005 |
| WO | WO 2005/049075 | 6/2005 |
| WO | 2005/063816 | 7/2005 |
| WO | WO 2005/061707 | 7/2005 |
| WO | WO 2005/063299 A2 | 7/2005 |
| WO | WO 2005/117986 | 12/2005 |
| WO | WO 2006/074367 | 7/2006 |
| WO | 2005/100399 | 12/2006 |
| WO | WO 2007/005760 A1 | 1/2007 |
| WO | WO 2008/143702 A2 | 11/2008 |

OTHER PUBLICATIONS

Huang et al. (Biochemical Pharmacology 2006 vol. 71 p. 1635).*
Tepsiri et al. (World J Gastroenterol 2005 vol. 11 2748).*
Enard et al. (Science 2002 vol. 296 p. 340).*
Cobb et al (Crit Care Med 2002 vol. 30 p. 2711).*
Cheung et al (Nature Genetics 2003 vol. 33 p. 422 as cited on the IDS).*
Wu (Journal of pathology 2001 vol. 195 p. 53).*
Newton et al (Journal of Computational Biology 2001 vol. 8 p. 37).*
Stranger et al. ( Science 2007 vol. 315 pp. 848-853).*
Obrien et al. (Cancer Research 2008 vol. 68 p. 5380).*
Beeram et al. (Journal of Clinical Oncology 2007 ASCO Annual Meeting Proceedings vol. 25 No. 18S p. 1042).*
Li et al. (Cancer Research 2005 vol. 65 Supplement 9 p. 1456).*
Lambert et al. (Current Opinion in Phramacology 2005 vol. 5 p. 543).*
Marcom et al. (Breast Cacner Res Treat 2007 vol. 102 p. 43).*
European Patent Office Communication (issued in counterpart EP application No. 09719560.6) (dated Mar. 15, 2011).
Nahta et al., "The HER-2-targeting antibodies trastuzumab and pertuzumab synergistically inhibit the survival of breast cancer cells" *Cancer Research* 64(7):2343-2346 (Apr. 1, 2004).
Yang Liu, et al., "Expression profiling of ABC transporters in a drug-resistant breast cancer cell line using AmpArray" *Molecular Pharmacology* 68(2):430-438 (2005).
Noma, B. et al. Pancreatic cancer therapy strategy targeting multidrug resistance-associated proteins (MRPs), Journal of the Japanese Society of Gastroenterology vol. 103, special issue p. A984, 2006 (English translation).
Yasui, et. al., "Alteration in Copy Number of Genes as a Mechanism for Acquired Drug Resistance", Cancer Research, Feb. 2004, vol. 64, pp. 1403-1410.
Gillet, et. al., "Microarray Expression Profiling of ABC Transporters in Human Breast Cancer", Cancer Genomics & Proteomics, 2006, vol. 3, pp. 97-106.
Zelcer, et. al., Characterization of Drug Transport by the Human Multidrug Resistance Protein 3 (ABCC3) Journal of Biological Chemistry, 2001, vol. 276, No. 49, pp. 46400-46407.
Arato, Teruyo, "Chapter 13: Approval Review of Antibody Medicine", Mitsuyoshi Ueda (Ed.) *Frontier of Development of Antibody Medicine*, CMC Publishing, Jul. 2007, pp. 139-154 (in Japanese with English translation).

(Continued)

*Primary Examiner* — Katherine Salmon
(74) *Attorney, Agent, or Firm* — Traci Ropp; Benjamin C. Pelletier; Arnold & Porter Kaye Scholer LLP

(57) ABSTRACT

Methods and compositions are provided to determine if a cancer is resistant to treatment with anti-mitotic agents, including treatment with T-DM1. The methods relate to determining if the ABCC3 gene is amplified and/or overexpressed in the cancer.

2 Claims, 13 Drawing Sheets

(56) References Cited

OTHER PUBLICATIONS

Bender, et. al., "Evaluation and PK/PD modeling of the dose regimen chronomodulation of Trastuzumab-MC-vc-PAB-MMAF (Tmab-vc-MMAF) in tumor bearing mouse models", Molecular Cancer Therapeutics, 2007, vol. 6, Suppl. 11, p. C167.
Bronger, et al., "ABCC drug efflux pumps and organic anion uptakes transporters in human gliomas in the blood-tumor barrier," Cancer Res 2006, vol. 65, No. 24, pp. 11419-11428.
De Jonge, et. al., "Evidence based selection of housekeeping genes", PloS One, 2007, vol. 2, No. 9, p. e898.
Erickson, et. al., Antibody-maytansinoid conjugates are activated in targeted cancer cells by lysosomal degradation and linker-dependent intracellular processing, Cancer Research, 2006, vol. 55, No. 8, pp. 4426-4433.
Ghose, et. al., "Immunochemotherapy of cancer with chlorambucil-carrying antibody", Br. Med. J., 1972, vol. 3, No. 5825, pp. 495-499.
Guo et al., "Role of multidrug resistance transporters in the biological response to trastuzumab-cytotoxic drug conjugates," Abstract. Proceedings of the 101st Annual Meeting of the American Association for Cancer Research; Apr. 17-21, 2010; Washington, DC. Philadelphia (PA): AACR; Cancer Res 2010;70(8 Suppl):Abstract No. 618.
Hanna, et. al., "HER2 in situ hybridization in breast cancer: clinical implications of polysomy 17 and genetic heterogeneity", Modern Pathology, 2014, vol. 27, No. 1, pp. 4-18.
Highlights of prescribing information for Herceptin®, 2007 (4 pages).
Highlights of prescribing information for Kadcycla® (TDM-1), May 2015 (24 pages).
Huang, et al., "Vincristine transcriptional regulation of efflux drug transporters in carcinoma cell lines," Biochem Pharmacol. 2006, vol. 71, No. 12, 1695-1704.
Ito, et. al., "Novel clusters of highly expressed genes accompany genomic amplification in breast cancers", FEBS letters, 2007, vol. 581, No. 21, pp. 3909-3914.
Lambert, et. al., "Ado-trastuzumab emtansine (T-DM1): An antibody-drug conjugate (ASC) for HER-2 positive breast cancer", J. Med. Chem., 2014, vol. 57, No. 16, pp. 6949-6964.
Lambros, et. al., "Chromogenic and fluorescent in situ hybridization in breast cancer", Human Pathology, 2007, vol. 38, No. 8, pp. 1105-1122.
Lang, et. al., "Genetic polymorphisms in the multidrug resistance-associated protein 3 (ABCC3, MRP3) gene and relationship to its mRNA and protein expression in human liver", Pharmacogenetics and Genomics, 2004, vol. 14, No. 3, pp. 155-164.
Linenberger, et. al., "Multidrug-resistance phenotype and clinical responses to gemtuzumab ozogamicin", Blood, 2001, vol. 98, No. 4, pp. 988-994.
Marchio, et. al., "Does chromosome 17 cetrmoere copy number predict polysomy in breast cancer? A fluoroscience in situ hybridization and microarray-based CGH analysis", The Journal of Pathology, 2009, vol. 219, No. 1, pp. 16-24.
Matsui, et. al., "Reduced effect of gemtuzumab ozogamicin (CMA-676) on P-glycoprotein and/or CD34-positive leukemia cells and its restoration by multidrug resistance modifiers", Leukemia, 2002, vol. 16, No. 5, pp. 813-819.
Mazor, et. al., "chFRP5-ZZ-PE38, a large IgG-toxin immunoconjugate outperforms the corresponding smaller FRP5 (Fv)-ETA immunotoxin in eradicating ErbB2-expressing tumor xenografts", Cancer Letters, 2007, vol. 257, No. 1, pp. 124-135.
Naito, et. al., "Calicheamicin-conjugated humanized anti-CD33 monoclonal antibody (gemtuzumab zogamicin, CMA-676) shows ctocidal effect on CD33-positive leukemia cell lines, but is inactive on P-glycoprotein-expressing sublines", Leukemia, 2000, vol. 14, No. 8, pp. 1436-1443.
Nies, et al., "Expression of the multidrug resistance MRP2 MRP3 in human hepatocellular carcinoma," Int J Cancer 2001, vol. 94, No. 4, pp. 492-499.
Notice of Opposition by Bayer Intellectual Property GmbH and Bayer Pharma Aktiengesellschaft in Opposition of European Patent No. EP2260111 dated Mar. 13, 2016 (85 pages).
Pastuskovas, et. al., "Tissue distribution, metabolism, and excretion of the antibody-drug conjugate, Herceptin-monomethyl auristatin E in rats", Cancer Research, 2005, vol. 65, Suppl. 9, pp. 1195.
PathVysion™ HER-2 DNA Probe Kit, Package Insert, 2001 (13 pages).
Rau, S. et al., "Expressions of the multidrug resistance proteins MRP2 MRP3 in human cholangiocellular carcinomas," Eur J Clin Invest 2008, vol. 38 No. 2, pp. 134-142.
Ross, et. al., "Targeted therapies for cancer", Am. J. Clin. Pathol, 2004, vol. 122, pp. 598-609.
Scharma, et. al., "Antibody targeted drugs as cancer therapeutics", Nature Reviews: Drug Discovery, 2006, vol. 5, No. 2, pp. 147-159.
Scheffer, et al., "Specific detection of multidrug resistance proteins MRP1, MRP2, MRP3, MRP5 and MDR3 P-glycoprotein with a panel of monoclonal antibodies," Cancer Res 2000, vol. 60, pp. 5269-5277.
Sidorov, et. al., Non-Covalent Conjugation of Nanoparticles to Antibodies via Electrostatic Interactions—A Computational Model, Journal of Computational and Theoretical Nanoscience, 2007, vol. 4, No. 6, pp. 1103-1107.
Szakacs, et. al., "Targeting multidrug resistance in cancer", Nature Reviews: Drug Discovery, 2006, vol. 5, No. 3, pp. 219-234.
Tepsiri, et. al., "Drug sensitivity and drug resistance profiles of human intrahepatic cholangiocarcinoma cell lines", World Journal of Gastroenterology, 2005, vol. 11, No. 18, pp. 2748-2753.
Walter, et. al., "CD33 expression and P-glycoprotein-mediated drug efflux inversely correlate and predict clinical outcome in patients with acute myeloid leukemia treated with gemtuzumab ozogamicin monotherapy", Blood, 2007, vol. 109, No. 10, pp. 4168-4170.
Wolff, et. al., "American Society of Clinical Oncology/College of American Pathologists guideline recommendations for human epidermal growth factor receptor 2 testing in breast cancer", Archives of pathology & laboratory medicine, 2007, vol. 131, No. 1, pp. 18-43.
Young, et. al., "Expression of multidrug resistance protein-related genes in lung cancer: correlation with drug response", Clinical Cancer Research, 1999, vol. 5, No. 3, pp. 673-680.
Zeng, et. al., "Expression of multidrug resistance protein-3 (multispecific organic anion transporter-D) in human embryonic kidney 293 cells confers resistance to anticancer agents", Cancer Research, 1999, vol. 59, No. 23, pp. 5964-5967.

* cited by examiner

| Subject ID | ABCC3 Copy Number | CEP17 Copy Number | ABCC3/CEP17 Ratio | ABCC3 Amplification Status | Best Response (1=CR, 2=PR, 3=SD, 4=PD, 5=UE) | Confirmed Objective Response | FISH HER2 (30 or 60 Cell Count) | IHC Staining Intensity | HER2 RT-PCR Conc. Ratio to G6PDH |
|---|---|---|---|---|---|---|---|---|---|
| 1 | High | 2.07 | >7 | Highly Amplified | 4 | 4 | Positive | 3+ | 41.83 |
| 2 | High | 2.07 | >7 | Highly Amplified | 2 | 2 | Positive | 3+ | 40.37 |
| 3 | High | 2.05 | >7 | Highly Amplified | 2 | 2 | Positive | 2+ | 36.70 |
| 4 | 6.4 | 1.65 | 3.87 | Amplified | 3 | 3 | Positive | 1+ | 8.84 |
| 5 | 3.65 | 1.87 | 1.95 | Amplified | 3 | 3 | Negative | 2+ | 4.59 |
| 6 | 2.59 | 1.50 | 1.72 | Normal | 2 | 2 | Negative | 0 | 2.23 |
| 7 | 6.44 | 3.95 | 1.60 | Cluster Amplification | 4 | 4 | Borderline | 1+ | 2.32 |
| 8 | 4.17 | 2.67 | 1.56 | Normal | 2 | 2 | Positive | 1+ | 17.55 |
| 9 | 4.61 | 3.00 | 1.54 | Normal | 2 | 2 | Positive | 3+ | 38.04 |
| 10 | 3.71 | 2.54 | 1.46 | Normal | 2 | 2 | Positive | 2+ | |
| 11 | 3.81 | 2.65 | 1.43 | Normal | 2 | 2 | Positive | 0 | 5.69 |
| 12 | 6.35 | 4.50 | 1.41 | Normal | 2 | 2 | Positive | 1+ | |
| 13 | 2.93 | 2.11 | 1.38 | Normal | 2 | 2 | Positive | 3+ | 22.80 |
| 14 | 2.91 | 2.11 | 1.37 | Normal | 2 | 2 | Positive | 3+ | 6.24 |
| 15 | 4.47 | 3.73 | 1.19 | Normal | 2 | 2 | | 3+ | |
| 16 | 3.91 | 3.39 | 1.15 | Normal | 2 | 2 | Positive | 1+ | 14.43 |
| 17 | 2.77 | 2.56 | 1.08 | Normal | 2 | 2 | Positive | 1+ | 14.65 |
| 18 | 2.41 | 2.30 | 1.04 | Normal | 4 | 4 | Positive | 3+ | |
| 19 | 2.41 | 2.36 | 1.02 | Normal | 2 | 2 | Positive | 3+ | 19.31 |
| 20 | 4.03 | 4.00 | 1.00 | Normal | 2 | 3 | Positive | 3+ | 33.92 |

CR=Complete Response; PR=Partial Response; SD=Stable Disease; PD=Progressive Disease, UE=Unevaluable
G6PDH=Glucose-6-phosphate Dehydrogenase

| FIG. 11A | FIG. 11B |

FIG. 11A
Molecular Subtype and Sensitivity to Anti-Mitotic Drugs

| Cell Line Designation: | Gene Expression Profiling Subtype | HER2 Copy number qPCR | Std. Dev. | Composite Molecular Subtype |
|---|---|---|---|---|
| BT549 | Basal-like | 1.7 | 0.1 | Basal-like |
| CAL-120 | Basal-like | 2.2 | 0.4 | Basal-like |
| CAL-51 | Basal-like | 2.5 | 0.0 | Basal-like |
| CAL-85-1 | Basal-like | 1.2 | 0.0 | Basal-like |
| DU4475 | Basal-like | 3.4 | 1.0 | Basal-like |
| HCC-1143 | Basal-like | 1.8 | 0.1 | Basal-like |
| HCC-70 | Basal-like | 1.0 | 0.0 | Basal-like |
| HS 578T | Basal-like | 4.5 | 0.2 | Basal-like |
| MDA-MB-231 | Basal-like | 1.6 | 0.0 | Basal-like |
| MDA-MB-435S | Basal-like | 1.0 | 0.0 | Basal-like |
| MDA-MB-436 | Basal-like | 1.0 | 0.0 | Basal-like |
| MDA-MB-468 | Basal-like | 2.8 | 0.3 | Basal-like |
| MT-3 | Basal-like | 2.0 | 0.2 | Basal-like |
| AU565 | Luminal | 13.4 | 1.2 | Her 2 |
| BT474 | Luminal | 17.0 | 1.9 | Her 2 |
| EFM-192A | Luminal | 28.5 | 0.9 | Her 2 |
| HCC-1419 | Luminal | 49.9 | 0.6 | Her 2 |
| HCC-2218 | Luminal | 81.2 | 0.9 | Her 2 |
| MDA-MB-361 | Luminal | 13.9 | 0.8 | Her 2 |
| MDA-MB-453 | Luminal | 8.0 | 0.2 | Her 2 |
| UACC-812 | Luminal | 12.4 | 4.8 | Her 2 |
| ZR-75-30 | Luminal | 31.2 | 0.4 | Her 2 |
| CAL-148 | Basal-like | 1.5 | 0.1 | Luminal |
| CAMA-1 | Luminal | 3.3 | 0.4 | Luminal |
| EFM-19 | Luminal | 2.8 | 0.6 | Luminal |
| EVSA-T | Luminal | 2.8 | 0.2 | Luminal |
| HCC-1428 | Luminal | 1.0 | 0.0 | Luminal |
| KPL-1 | Luminal | 1.9 | 0.2 | Luminal |
| MCF-7 | Luminal | 1.3 | 0.1 | Luminal |
| T47D | Luminal | 2.1 | 0.1 | Luminal |
| ZR-75-1 | Luminal | 1.3 | 0.0 | Luminal |

FIG. 11B

| MMAE IC50 (nM)[1] | Std. Dev. MMAE[2] | Paclitaxel IC50 (nM) | Std. Dev. Paclitaxel |
|---|---|---|---|
| 4.6 | 2.2 | 5.5 | 14.1 |
| 17.2 | 4.8 | 11.4 | 12.4 |
| 1.3 | 2.1 | 12.8 | 7.6 |
| 2.1 | 4.1 | 1.7 | 9.2 |
| 1.5 | 3.9 | 133.6 | 31.8 |
| >100 | NA | 7.4 | 5.8 |
| 1.1 | 5.6 | 17.9 | 11.3 |
| 0.9 | 0.3 | 42.5 | 29.3 |
| 38.9 | 6.0 | 9.8 | 8.6 |
| 0.6 | 0.4 | 1.0 | 1.0 |
| 1.9 | 0.6 | >1000 | NA |
| 0.5 | 0.5 | 0.52 | 17.3 |
| 10.4 | 18.2 | 90.1 | 51.1 |
| 0.3 | 0.2 | 4.0 | 10.3 |
| >100 | NA | >1000 | NA |
| >100 | NA | >1000 | NA |
| >100 | NA | >1000 | NA |
| >100 | NA | >1000 | NA |
| >100 | NA | >1000 | NA |
| >100 | NA | >1000 | NA |
| >100 | NA | >1000 | NA |
| >100 | NA | >1000 | NA |
| 2.4 | 1.3 | 12.8 | 9.4 |
| 0.2 | 0.5 | 2.8 | 3.7 |
| 0.4 | 0.3 | 18.4 | 16.4 |
| 2.0 | 10.1 | >1000 | NA |
| >100 | NA | >1000 | NA |
| >100 | NA | >1000 | NA |
| 2.7 | 4.5 | 0.1 | 1.2 |
| >100 | NA | 0.1 | 1.2 |
| >100 | NA | >1000 | NA |

[1] >100 (MMAE), >1000 (paclitaxel) indicates $IC_{50}$ was not achieved in this cell line due to less than 50% inhibition of cell viability

[2] NA, Not applicable as cell line did not achieve $IC_{50}$

SEQUENCE LISTING

```
<160> NUMBER OF SEQ ID NOS: 6

<210> SEQ ID NO 1
<211> LENGTH: 21
<212> TYPE: DNA
<213> ORGANISM: ARTIFICIAL SEQUENCE
<220> FEATURE:
<223> OTHER INFORMATION: SYNTHETIC OLIGONUCLEOTIDE PRIMER

<400> SEQUENCE: 1
cactgtctgc accttgcttt g                                              21

<210> SEQ ID NO 2
<211> LENGTH: 24
<212> TYPE: DNA
<213> ORGANISM: ARTIFICIAL SEQUENCE
<220> FEATURE:
<223> OTHER INFORMATION: SYNTHETIC OLIGONUCLEOTIDE PRIMER

<400> SEQUENCE: 2
gctctgcagc tattgaaaga acaa                                           24

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC OLIGONUCLEOTIDE PRIMER
```

```
<400> SEQUENCE: 3
aaagccgctc aactacatgg                                               20

<210> SEQ ID NO 4
<211> LENGTH: 21
<212> TYPE: DNA
<213> ORGANISM: ARTIFICIAL SEQUENCE
<220> FEATURE:
<223> OTHER INFORMATION: SYNTHETIC OLIGONUCLEOTIDE PRIMER

<400> SEQUENCE: 4
tgctttgaat gcgtcccaga g                                             21

<210> SEQ ID NO 5
<211> LENGTH: 19
<212> TYPE: DNA
<213> ORGANISM: ARTIFICIAL SEQUENCE
<220> FEATURE:
<223> OTHER INFORMATION: SYNTHETIC OLIGONUCLEOTIDE PRIMER

<400> SEQUENCE: 5
gattccagcc gcttcagtt                                                19

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: SYNTHETIC OLIGONUCLEOTIDE PRIMER

<400> SEQUENCE: 6
cctggctgtg ctctacacct                                               20
```

GENETIC VARIATIONS ASSOCIATED WITH DRUG RESISTANCE

This application claims the benefit of priority to U.S. Provisional Application Ser. No. 61/036,874 filed on 14 Mar. 2008 and U.S. Provisional Application Ser. No. 61/054,064 filed on 16 May 2008, both of which are incorporated by reference in their entirety herein.

FIELD OF THE INVENTION

The present invention generally relates to genetic variations that are predictive of drug resistance.

BACKGROUND

A key goal of modern molecular oncology is identifying the underlying genetic and genomic variations that characterize a given tumor so that the patient can receive targeted therapy with chemotherapeutic agents likely to provide the most benefit. Breast cancer is the most common form of cancer among women in the Western World, with an estimated 1 million new diagnoses and 400,000 deaths per year worldwide (1). The advent of targeted therapies such as Tamoxifen for estrogen receptor positive cancer (2) and Herceptin for tumors harboring amplification of the HER2 oncogene (3) has had significant impact on patient survival, yet various chemotherapy regimens still form an important component of breast cancer treatment (4). Breast cancer is a heterogeneous disease with distinct molecular subtypes characterized by differential response to targeted and chemotherapeutic agents. While chemotherapy is a successful treatment regimen in many cases, an estimated 50% of patients fail to benefit due to intrinsic or acquired multidrug resistance (1). Multidrug resistance (MDR) refers to the resistance of cancer cells to multiple classes of chemotherapeutic drugs that can be structurally and mechanistically unrelated and is related to the overexpression of a variety of proteins that act as ATP-dependent efflux pumps (5). Understanding the molecular alterations that contribute to MDR in breast cancer is a crucial first step in enabling the development of diagnostic tests capable of predicting resistance to a given therapy and rationally selecting more efficacious therapeutic agents.

ABCC3 overexpression has been implicated in acquired multidrug resistance in cancer cell lines in previous studies. For instance, Liu et al report 459-fold overexpression of ABCC3 relative to the parental in a cell line, MCF-7/AdVp3000, that was derived by selection for growth in the presence of doxorubicin (36). In addition, it has recently been shown that treatment of carcinoma cell lines with vincristine results in significant upregulation of ABCC2 and ABCC3 transcripts in these cells (37). The related pumps ABCC2(MRP2) and ABCC10 (MRP7) have both been shown to confer paclitaxel resistance when overexpressed (38) (39), and ABCC2 has been shown to be an important determinant of paclitaxel pharmacokinetics in vivo in mouse models (40). Paclitaxel has not been previously demonstrated to be a substrate for ABCC3 and indeed studies of ectopic overexpression of ABCC3 in MDCK or NIH-3T3 cells have failed to demonstrate increased resistance to paclitaxel (41, 42). Notably, it was also found (41) that ABCC3 cannot confer resistance to doxorubicin in long term assays despite other published reports of functional studies suggesting a role for ABCC3 in transporting this agent (36).

These various observations illustrate the fact that breast cancer is a heterogeneous disease that can evade chemotherapy through multiple mechanisms and highlight the need for panels of biomarkers that can be used to predict therapeutic response in individual cancer patients.

SUMMARY OF THE INVENTION

One aspect of the present invention provides for a method for determining whether a cancer in a patient is resistant to treatment with an anti-mitotic agent, comprising detecting whether the ABCC3 gene is amplified in a test cancer sample from the patient, wherein amplification of the ABCC3 gene indicates that the cancer is resistant to treatment with the anti-mitotic agent. In one embodiment, the test cancer sample is a cancer tumor sample.

The amplification of the ABCC3 gene is detected, for example, by determining the copy number of the ABCC3 gene. In some embodiments a copy number of at least 3 indicates ABCC3 gene amplification, in other embodiments, a copy number of at least 5 indicates ABCC3 gene amplification.

The copy number of the ABCC3 gene is determined, for example, by fluorescence in situ hybridization (FISH), Southern Blot, immunohistochemisty (IHC), polymerase chain reaction (PCR), quantitative PCR (qPCR), quantitative real-time PCR (qRT-PCR), comparative genomic hybridization, microarray based comparative genomic hybridization, or ligase chain reaction (LCR).

Another aspect of the invention provides for a method for determining whether a cancer in a patient is resistant to treatment with an anti-mitotic agent, comprising detecting whether the ABCC3 gene is overexpressed in a test cancer sample from the patient, wherein overexpression of the ABCC3 gene indicates that the cancer is resistant to treatment with the anti-mitotic agent.

In one embodiment, overexpression of the ABCC3 gene is detected by determining the level of mRNA transcription from the ABCC3 gene. In some embodiments, overexpression of the ABCC3 gene is indicated by an at least 5-fold increase in mRNA transcription level from the ABCC3 gene in the test cancer sample relative to a control sample. In other embodiments, overexpression of the ABCC3 gene is indicated by an at least 25-fold increase in mRNA transcription level from the ABCC3 gene in the test cancer sample relative to a control sample.

In another embodiment, overexpression of the ABCC3 gene is detected by determining the level of ABCC3 polypeptide expression. In some embodiments, the level of ABCC3 polypeptide expression comprises contacting the test cancer sample with an anti-ABCC3 antibody and detecting binding of the anti-ABCC3 antibody to ABCC3 polypeptide. In some embodiments, overexpression of the ABCC3 gene is indicated by an at least 2-fold increase in the level of expression of ABCC3 polypeptide in the test cancer sample relative to a control sample. In other embodiments, overexpression of the ABCC3 gene is indicated by an at least 10-fold increase in the level of expression of ABCC3 polypeptide in the test cancer sample relative to a control sample.

In some embodiments, the cancer is selected from the group consisting of breast cancer, ovarian cancer, and colorectal cancer.

In some embodiments, the anti-mitotic agent is selected from the group consisting of taxanes (including, for example paclitaxel and docetaxel), maytansinoids (including, for example, DM1 and DM4), and auristatins (including, for example, monomethyl auristatin E (MMAE) and monomethyl auristatin F (MMAF)), and analogs and derivatives thereof.

In some embodiments, the anti-mitotic agent is conjugated to an antibody. In one embodiment, the anti-mitotic agent-antibody conjugate is a maytansinoid-anti-Her2 antibody conjugate, such as trastuzumab-DM1.

Another aspect of the invention provides for a method for determining whether a breast cancer tumor is resistant to treatment with an anti-mitotic agent, comprising detecting whether the ABCC3 gene is amplified in a breast cancer tumor sample, wherein amplification of the ABCC3 gene indicates that the breast cancer tumor is resistant to treatment with the anti-mitotic agent.

The amplification of the ABCC3 gene is detected, for example, by determining the copy number of the ABCC3 gene. In some embodiments a copy number of at least 3 indicates ABCC3 gene amplification, in other embodiments, a copy number of at least 5 indicates ABCC3 gene amplification.

The copy number of the ABCC3 gene is determined, for example, by fluorescence in situ hybridization (FISH), Southern Blot, immunohistochemisty (IHC), polymerase chain reaction (PCR), quantitative PCR (qPCR), quantitative real-time PCR (qRT-PCR), comparative genomic hybridization, microarray based comparative genomic hybridization, or ligase chain reaction (LCR).

Another aspect of the invention provides for a method for determining whether a breast cancer tumor is resistant to treatment with an anti-mitotic agent, comprising detecting whether the ABCC3 gene is overexpressed in a breast cancer tumor sample, wherein overexpression of the ABCC3 gene indicates that the breast cancer tumor is resistant to treatment with the anti-mitotic agent.

In one embodiment, overexpression of the ABCC3 gene is detected by determining the level of mRNA transcription from the ABCC3 gene. In some embodiments, overexpression of the ABCC3 gene is indicated by an at least 5-fold increase in mRNA transcription level from the ABCC3 gene in the test cancer sample relative to a control sample. In other embodiments, overexpression of the ABCC3 gene is indicated by an at least 25-fold increase in mRNA transcription level from the ABCC3 gene in the test cancer sample relative to a control sample.

In another embodiment, overexpression of the ABCC3 gene is detected by determining the level of ABCC3 polypeptide expression. In some embodiments, the level of ABCC3 polypeptide expression comprises contacting the test cancer sample with an anti-ABCC3 antibody and detecting binding of the anti-ABCC3 antibody to ABCC3 polypeptide. In some embodiments, overexpression of the ABCC3 gene is indicated by an at least 2-fold increase in the level of expression of ABCC3 polypeptide in the test cancer sample relative to a control sample. In other embodiments, overexpression of the ABCC3 gene is indicated by an at least 10-fold increase in the level of expression of ABCC3 polypeptide in the test cancer sample relative to a control sample.

In some embodiments, the breast cancer tumor is a Her-2 positive breast cancer tumor.

In some embodiments, the anti-mitotic agent is selected from the group consisting of taxanes (including, for example paclitaxel and docetaxel), maytansinoids (including, for example, DM1 and DM4), and auristatins (including, for example, monomethyl auristatin E (MMAE) and monomethyl auristatin F (MMAF)), and analogs and deriviatives thereof.

In some embodiments, the anti-mitotic agent is conjugated to an antibody. In one embodiment, the anti-mitotic agent-antibody conjugate is a maytansinoid-anti-Her2 antibody conjugate, such as trastuzumab-DM1.

Another aspect of the invention provides for a method for selecting a breast cancer patient for anti-mitotic agent-based chemotherapy comprising a) detecting whether the ABCC3 gene is amplified in a test cancer sample from the patient, and b) selecting the patient for anti-mitotic drug-based chemotherapy if amplification of the ABCC3 gene is not detected in the test cancer sample.

The amplification of the ABCC3 gene is detected, for example, by determining the copy number of the ABCC3 gene. In some embodiments a copy number of at least 3 indicates ABCC3 gene amplification, in other embodiments, a copy number of at least 5 indicates ABCC3 gene amplification.

The copy number of the ABCC3 gene is determined, for example, by fluorescence in situ hybridization (FISH), Southern Blot, immunohistochemisty (IHC), polymerase chain reaction (PCR), quantitative PCR (qPCR), quantitative real-time PCR (qRT-PCR), comparative genomic hybridization, microarray based comparative genomic hybridization, or ligase chain reaction (LCR).

Another aspect of the invention provides for a method for selecting a breast cancer patient for anti-mitotic agent-based chemotherapy comprising a) detecting whether the ABCC3 gene is overexpressed in a test cancer sample from the patient, and b) selecting the patient for anti-mitotic drug-based chemotherapy if overexpression of the ABCC3 gene is not detected in the test cancer sample.

In one embodiment, overexpression of the ABCC3 gene is detected by determining the level of mRNA transcription from the ABCC3 gene. In some embodiments, overexpression of the ABCC3 gene is indicated by an at least 5-fold increase in mRNA transcription level from the ABCC3 gene in the test cancer sample relative to a control sample. In other embodiments, overexpression of the ABCC3 gene is indicated by an at least 25-fold increase in mRNA transcription level from the ABCC3 gene in the test cancer sample relative to a control sample.

In another embodiment, overexpression of the ABCC3 gene is detected by determining the level of ABCC3 polypeptide expression. In some embodiments, the level of ABCC3 polypeptide expression comprises contacting the test cancer sample with an anti-ABCC3 antibody and detecting binding of the anti-ABCC3 antibody to ABCC3 polypeptide. In some embodiments, overexpression of the ABCC3 gene is indicated by an at least 2-fold increase in the level of expression of ABCC3 polypeptide in the test cancer sample relative to a control sample. In other embodiments, overexpression of the ABCC3 gene is indicated by an at least 10-fold increase in the level of expression of ABCC3 polypeptide in the test cancer sample relative to a control sample.

In some embodiments, the breast cancer patient has Her-2 positive breast cancer.

In some embodiments, the anti-mitotic agent is selected from the group consisting of taxanes (including, for example paclitaxel and docetaxel), maytansinoids (including, for example, DM1 and DM4), and auristatins (including, for example, monomethyl auristatin E (MMAE) and monomethyl auristatin F (MMAF)), and analogs and deriviatives thereof.

In some embodiments, the anti-mitotic agent is conjugated to an antibody. In one embodiment, the anti-mitotic agent-antibody conjugate is a maytansinoid-anti-Her2 antibody conjugate, such as trastuzumab-DM1.

Another aspect of the invention provides for a method of reducing resistance of a cancer cell to an anti-mitotic agent comprising contacting the cancer cell with an antagonist of ABCC3. In some embodiments, the antagonist is an ABCC3 antibody or an siRNA that binds to ABCC3.

Yet another aspect of the invention provides for a method of treating a patient with a cancer that is resistant to anti-mitotic agents comprising administering to the patient an antagonist of ABCC3 and an therapeutically effective amount of an anti-mitotic agent. In some embodiments, the antagonist is an ABCC3 antibody or an siRNA that binds to ABCC3. In some embodiments, the anti-mitotic agent is selected from the group consisting of taxanes, maytansinoids, and auristatins, and analogs and deriviatives thereof. In some embodiments, the anti-mitotic agent is conjugated to an antibody. In one embodiment, the anti-mitotic agent-antibody conjugate is a maytansinoid-anti-Her2 antibody conjugate, such as trastuzumab-DM1.

The invention also provides methods of treating cancer patients based on the ABCC3 amplification status of their cancer. In one embodiment, the method comprises detecting whether the ABCC3 gene is amplified or overexpressed in a test cancer sample from the patient and administering to the patient a therapeutically effective amount of an anti-mitotic drug-based chemotherapy if amplification or overexpression of the ABCC3 gene is not detected in the test cancer sample. In one embodiment, the patient has Her2 positive breast cancer and is administered an anti-Her2 antibody-anti-mitotic agent conjugate such as trastuzumab-DM1 or trastuzumab-MMAE.

In another aspect of the invention, a patient is selected for anti-mitotic drug-based chemotherapy based on absence of ABCC3 amplification or overexpression in their cancer and administered a therapeutically effective amount of an anti-mitotic drug. In one embodiment, the selected patient has Her2 positive breast cancer and is administered an anti-Her2 antibody-anti-mitotic agent conjugate such as trastuzumab-DM1 or trastuzumab-MMAE.

BRIEF DESCRIPTION OF THE FIGURES

FIG. 10 shows the result of a FISH analysis performed on samples obtained from a T-DM1 Phase II trial.

FIG. 11 is a Table showing information on molecular subtype of cell lines and their sensitivity to anti-mitotic drugs.

DETAILED DESCRIPTION OF EMBODIMENTS

I. Definitions

Figure 1A:
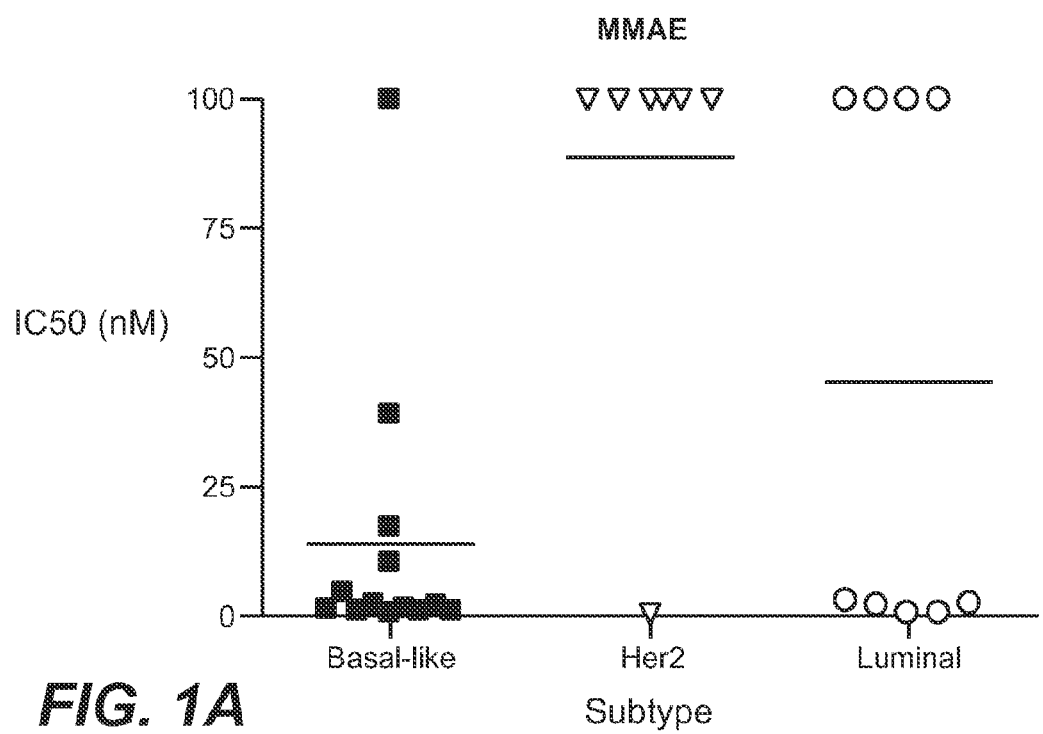
FIG. 1a illustrates an in vitro response of breast cancer cell lines to MMAE.

The phrases "gene amplification" and "gene duplication" (and variants such as "amplification of a gene" or "duplication of a gene") are used interchangeably and refer to a process by which multiple copies of a gene or gene fragment are formed in a particular cell or cell line. The duplicated region (a stretch of amplified DNA) is often referred to as an "amplicon." Usually, the amount of the messenger RNA (mRNA) produced, i.e., the level of gene expression, also increases in proportion to the number of copies made of the particular gene.

The term "ABCC3," as used herein, refers to any native ABCC3 (also known as MRP-3) from any vertebrate source, including mammals such as primates (e.g. humans and monkeys) and rodents (e.g., mice and rats), unless otherwise indicated. The term encompasses "full-length," unprocessed ABCC3 as well as any form of ABCC3 that results from processing in the cell. The term also encompasses naturally occurring variants of ABCC3, e.g., splice variants, allelic variants, and other isoforms. The term also encompasses fragments or variants of a native ABCC3 that maintain at least one biological activity of ABCC3. Examples of ABCC3s include those identified with Genbank accession numbers NM_003786 (human) and XM_358306 (mouse). See also, Kiuchi, et al., FEBS Lett. 433:149-152 (1998); and Borst, et al., JNCI 92(16):1295-1302 (2000).

The term "genetic variation" includes variations in the amplification of a gene or polypeptide as well as variations in an amino acid sequence or polynucleotide sequence.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

A cancer patient who "responds to treatment" or is "responsive to treatment" with an anti-mitotic is one that shows clinical or therapeutic benefit from or as a result of the treatment with the anti-mitotic agent. Such benefit includes cellular or biological responses, a complete response, a partial response, a stable disease (without progression or relapse), or a response of the patient from or as a result of the treatment with the agent with a later relapse.

A cancer, cancer cell, or cancer tumor that is "resistant to treatment" with an anti-mitotic agent is one that does not show a statistically significant cellular or biological response to the agent. Conversely, cancer, cancer cells, or cancer tumors that are not resistant to treatment with the agent show statistically significant cellular or biological responses to the agent such as, for example, an increase in the rate of cell death, or apoptosis, or decrease in proliferation or growth as compared to cancer cells or tumors that have not been treated with the agent. In specific embodiments, a cancer, cancer cell, or cancer tumor is resistant to treatment with MMAE if the IC50 is greater than 30 nM, or alternatively greater than 50 nM, or alternatively greater than 100 nM of MMAE. In other embodiments, a cancer, cancer cell, or cancer tumor is resistant to treatment with paclitaxel if the IC50 is greater than 50 nM, or alternatively greater than 100 nM, or alternatively greater than 500 nM, or alternatively greater than 1000 nM of paclitaxel.

An "anti-mitotic agent" is a compound that inhibits, prevents, or otherwise disrupts mitosis. Specific examples of anti-mitotic agents include, but are not limited to, taxanes, such as paclitaxel and docetaxel; maytansinoids, such as DM1 and DM4; dolastatin 10; dolastatin 15; auristatins, such as monomethyl auristatin E (MMAE) and monomethyl auristatin F (MMAF); vinca alkoloids, such as vinblastine and vincristine; and analogs and deriviatives thereof. The anti-mitotic agent is optionally conjugated to an antibody.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

An "individual" or a "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a patient is a human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A "tumoricidal" agent causes destruction of tumor cells.

A "toxin" is any substance capable of having a detrimental effect on the growth or proliferation of a cell.

A "chemotherapeutic agent" is a chemical compound useful in the treatment of cancer.

The term "antagonist" is used in the broadest sense, and includes any molecule that partially or fully blocks, inhibits, or neutralizes a biological activity of a polypeptide, such as ABCC3, or the transcription or translation thereof. Suitable antagonist molecules include, but are not limited to, antagonist antibodies, polypeptide fragments, oligopeptides, organic molecules (including small molecules), and antisense nucleic acids, including siRNA.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The term "anti-ABCC3 antibody" or "an antibody that binds to ABCC3" refers to an antibody that is capable of binding ABCC3 with sufficient affinity such that the antibody is useful as a diagnostic and/or therapeutic agent in targeting ABCC3. Preferably, the extent of binding of an anti-ABCC3 antibody to an unrelated, non-ABCC3 protein is less than about 10% of the binding of the antibody to ABCC3 as measured, e.g., by a radioimmunoassay (RIA). In certain embodiments, an antibody that binds to ABCC3 has a dissociation constant (Kd) of ≤1 µM, ≤100 nM, ≤10 nM, ≤1 nM, or ≤0.1 nM. In certain embodiments, an anti-ABCC3 antibody binds to an epitope of ABCC3 that is conserved among ABCC3 from different species.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example, one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is a minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO93/1161; Hudson et al. (2003) *Nat. Med.* 9:129-134; and Hollinger et al., Proc. Natl. Acad. Sci. USA 90: 6444-6448 (1993). Triabodies and tetrabodies are also described in Hudson et al. (2003) *Nat. Med.* 9:129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., *Antibodies: A Laboratory Manual*, (Cold Spring Harbor Laboratory Press, $2^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage display technologies (see, e.g., Clackson et al., Nature, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., *Proc. Natl. Acad. Sci. USA* 90: 2551 (1993); Jakobovits et al., Nature 362: 255-258 (1993); Bruggemann et al., *Year in Immunol.* 7:33 (1993); U.S. Pat. Nos. 5,545,807; 5,545,806; 5,569,825; 5,625,126; 5,633,425; 5,661,016; Marks et al., *Bio. Technology* 10: 779-783 (1992); Lonberg et al., Nature 368: 856-859 (1994); Morrison, Nature 368: 812-813 (1994); Fishwild et al., *Nature Biotechnol.* 14: 845-851 (1996); Neuberger, *Nature Biotechnol.* 14: 826 (1996) and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al., *J. Mol. Biol.*, 222: 581-597 (1991) and Hoogenboom et al., *Nucl. Acids Res.*, 19: 4133-4137 (1991)); using human myeloma and mouse-human heteromyeloma cell lines for the production of human monoclonal antibodies (see, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991)); and generating monoclonal antibodies in transgenic animals (e.g., mice) that are capable of producing a full repertoire of human antibodies in the absence of endogenous immunoglobulin production (see, e.g., Jakobovits et al., *Proc. Natl. Acad. Sci. USA*, 90: 2551 (1993); Jakobovits et al., Nature, 362: 255 (1993); Bruggermann et al., *Year in Immunol.*, 7: 33 (1993)). This definition of a human antibody specifically excludes a humanized antibody comprising antigen-binding residues from a non-human animal.

An "affinity matured" antibody is one with one or more alterations in one or more CDRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of HVR and/or framework residues is described by: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al., *J. Mol. Biol.* 226:889-896 (1992).

A "blocking" antibody or an "antagonist" antibody is one which inhibits or reduces a biological activity of the antigen it binds. Certain blocking antibodies or antagonist antibodies partially or completely inhibit the biological activity of the antigen.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain (see Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known. Binding to human FcRn in vivo and serum half life of human FcRn high affinity binding polypeptides can be assayed, e.g., in transgenic mice or transfected human cell lines expressing human FcRn, or in primates administered with Fc variant polypeptides.

WO00/42072 (Presta) describes antibody variants with improved or diminished binding to FcRs. The content of that patent publication is specifically incorporated herein by reference. See, also, Shields et al. *J. Biol. Chem.* 9(2): 6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils. The effector cells may be isolated from a native source, e.g., from blood.

"Antibody-dependent cell-mediated cytotoxicity" or "ADCC" refers to a form of cytotoxicity in which immunoglobulin bound to Fc receptors (FcRs) present on certain cytotoxic effector cells (e.g. Natural Killer (NK) cells, neutrophils, and macrophages) enables those cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

The term "Fc region-comprising polypeptide" refers to a polypeptide, such as an antibody or immunoadhesin, which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

A "cytotoxic antibody" is an antibody that is capable of an effector function and/or inducing cell death upon binding to its target antigen.

An "immunoconjugate" or "antibody conjugate" refers to an antibody conjugated to one or more cytotoxic agents.

A "small molecule" or "small organic molecule" is defined herein as an organic molecule having a molecular weight below about 500 Daltons.

An "ABCC3-binding oligopeptide" or an "oligopeptide that binds ABCC3" or "ABCC3 polypeptide binding oligopeptide" is an oligopeptide that is capable of binding ABCC3 with sufficient affinity such that the oligopeptide is useful as a diagnostic and/or therapeutic agent in targeting ABCC3. In certain embodiments, the extent of binding of an ABCC3-binding oligopeptide to an unrelated, non-ABCC3 protein is less than about 10% of the binding of the ABCC3-binding oligopeptide to ABCC3 as measured, e.g., by a surface plasmon resonance assay. In certain embodiments, an ABCC3-binding oligopeptide has a dissociation constant (Kd) of ≤1 μM, ≤100 nM, ≤10 nM, ≤1 nM, or ≤0.1 nM.

An "ABCC3-binding organic molecule" or "an organic molecule that binds ABCC3" or "ABCC3 polypeptide binding organic molecule" is an organic molecule other than an oligopeptide or antibody as defined herein that is capable of binding ABCC3 with sufficient affinity such that the organic molecule is useful as a diagnostic and/or therapeutic agent in targeting ABCC3. In certain embodiments, the extent of binding of an FGFR2-binding organic molecule to an unrelated, non ABCC3 protein is less than about 10% of the binding of the ABCC3-binding organic molecule to ABCC3 as measured, e.g., by a surface plasmon resonance assay. In certain embodiments, an ABCC3-binding organic molecule has a dissociation constant (Kd) of ≤1 μM, ≤100 nM, ≤10 nM, ≤1 nM, or ≤0.1 nM.

The dissociation constant (Kd) of any molecule that binds a target polypeptide may conveniently be measured using a surface plasmon resonance assay. Such assays may employ a BIAcore™-2000 or a BIAcore™-3000 (BIAcore, Inc., Piscataway, N.J.) at 25° C. with immobilized target polypeptide CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Target polypeptide is diluted with 10 mM sodium acetate, pH 4.8, to 5 μg/ml (~0.2 μM) before injection at a flow rate of 5 μl/minute to achieve approximately 10 response units (RU) of coupled protein. Following the injection of target polypeptide, 1 M ethanolamine is injected to block unreacted groups. For kinetics measurements, two-fold serial dilutions of the binding molecule (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgrams. The equilibrium dissociation constant (Kd) is calculated as the ratio $k_{off}/k_{on}$. See, e.g., Chen, Y., et al., (1999) *J. Mol. Biol.* 293:865-881. If the on-rate of an antibody exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

The word "label" when used herein refers to a detectable compound or composition. The label may be detectable by itself (e.g., radioisotope labels or fluorescent labels) or, in the case of an enzymatic label, may catalyze chemical alteration of a substrate compound or composition which results in a detectable product. Radionuclides that can serve as detectable labels include, for example, I-131, I-123, I-125, Y-90, Re-188, Re-186, At-211, Cu-67, Bi-212, and Pd-109.

An "isolated" biological molecule, such as a nucleic acid, polypeptide, or antibody, is one which has been identified and separated and/or recovered from at least one component of its natural environment.

II. Description of Certain Embodiments

Primary breast tumors may be classified into at least three major subtypes by gene expression profiling and the subtypes have different prognostic outcomes in terms of patient survival (9). Luminal breast cancers are typically estrogen receptor positive and characterized by coordinate expression of a number of epithelial specific genes, a relatively good prognosis, and good response rates to targeted hormonal therapies. HER2 positive breast cancers are characterized by high level gene amplification of the HER2 oncogene, relatively poor prognosis if untreated, and significant clinical benefit from the HER2 targeting monoclonal antibody Trastuzumab (Herceptin, Genentech) (3). Basal-like breast cancers typically lack expression of HER2, ER and progesterone receptor and hence are sometimes referred to as "triple negative" tumors (10, 11). Basal-like breast cancers have a relatively poor prognosis and currently have not been shown to respond to any targeted therapy (12). Theses subtypes display differential response to preoperative chemotherapy regimens (13) but for the most part the drug resistance mechanisms underlying these differences have yet to be determined.

Recent studies have revealed that large collections of breast cancer cell lines reflect many of the genetic and genomic changes characteristic of human breast tumors and hence may serve as a model system for a population of molecularly heterogeneous breast cancers (14). For instance cells may be classified into basal-like and luminal subtypes based on gene expression profiling signatures, and they retain most of the high-level amplifications and deletions that are associated with poor outcome in primary tumors (14).

Molecular classification of breast cancers into subtypes with shared features and similar prognostic outcomes provides a framework to begin efforts to individualize cancer therapy. The present invention demonstrates that breast cancer subtypes show clear differences in response to anti-mitotic agents, with the basal-like subtype being the most sensitive. One mechanism for this differential response is amplification of the ABCC3 drug efflux pump that was observed in a subset of luminal and HER2 amplified cell lines but not in basal-like cell lines.

As described in the Examples, the present invention utilized a panel of breast cancer cell lines molecularly characterized as a model for pharmacogenomic analysis to identify resistance mechanisms and subtype differences in response to two anti-mitotic based therapeutics, monomethyl-auristatin-E (MMAE) and paclitaxel. MMAE is structurally related to dolastatin 10, a pentapeptide natural product that has been the subject of several human clinical trials for cancer therapy, and exhibits potent antitumor activities by inhibiting tubulin polymerization and thus destabilize cellular microtubules (15). Auristatin-monoclonal antibody conjugates have been developed with the rationale that targeted delivery of the drug through specific antigen recognition by the antibody will lead to enhanced chemotherapeutic efficacy while sparing non-target expressing tissues from toxicity (15). Paclitaxel and the related compound docetaxel are anticancer cytotoxic drugs that stabilize microtubules and are widely used in the treatment of breast cancer (16).

Figure 6A:
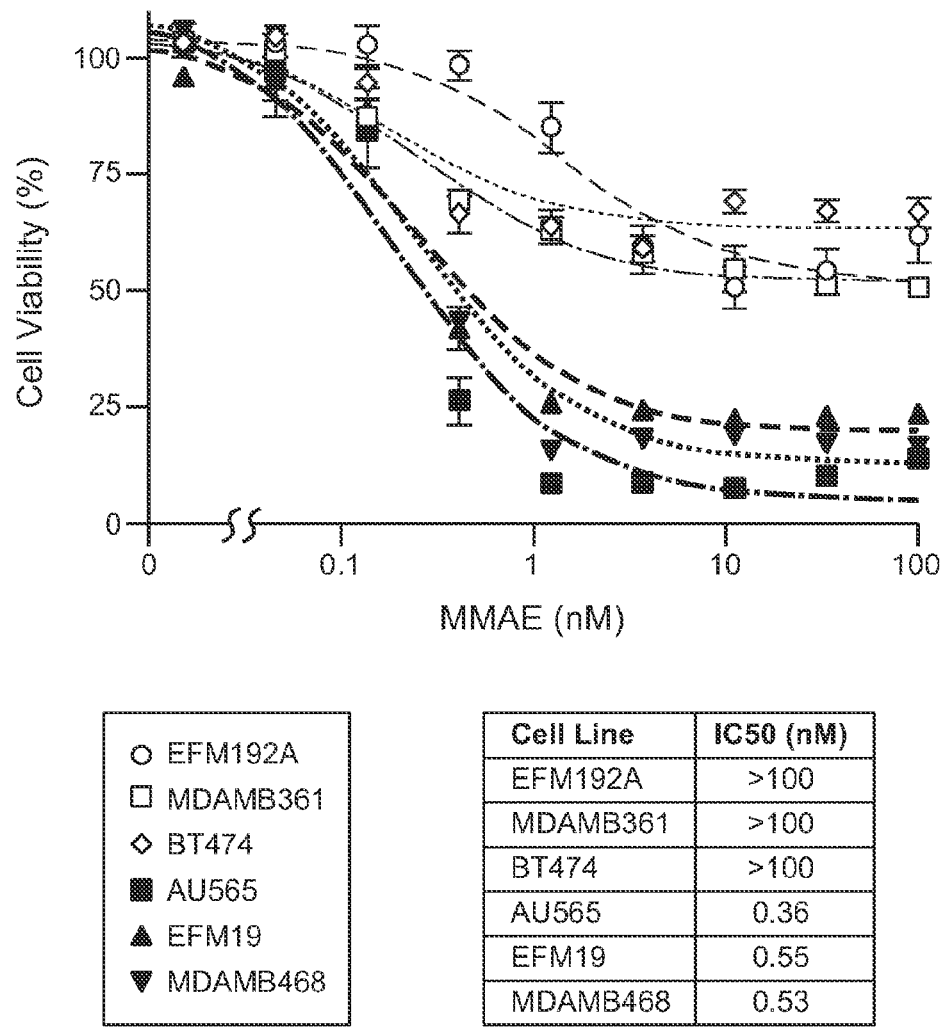
FIG. 6 shows growth inhibition of breast cancer cell lines treated with either MMAE (a) or paclitaxel (b). Points represent the average of four replicate wells in a 384-well plate with fitted nonlinear dose-response curves. The y-axis indicates the percent cell viability relative to control vehicle treated wells. Error bars indicate standard deviations.
Figure 6B:
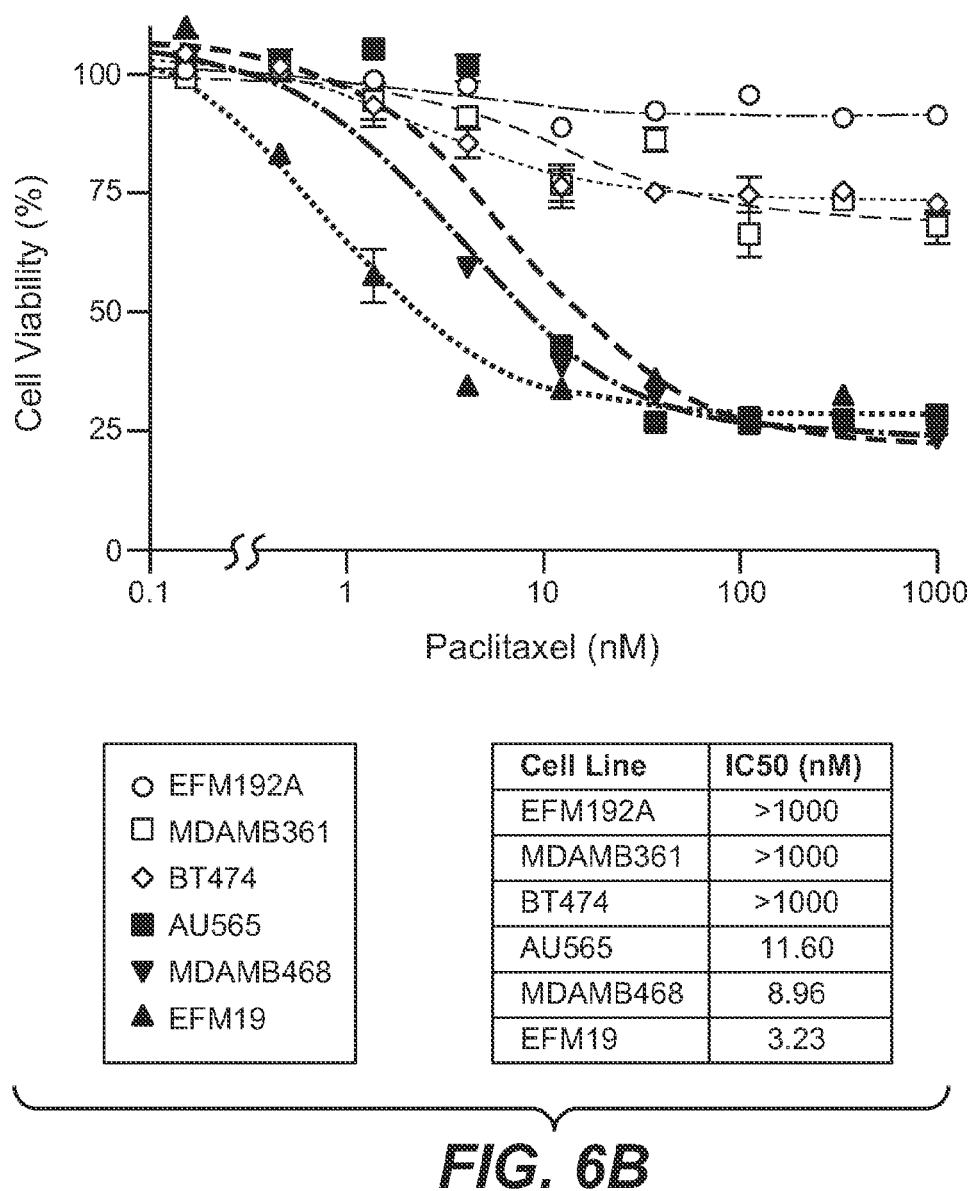

Based on these studies set forth in the Examples, amplification of a region of chromosome 17 (17q21) was found to be strongly associated with in vitro resistance to taxanes and auristatins. The region of amplification harbors at least 100 genes. In order to identify the relevant gene, an unbiased approach consisting of RNA interference and high content analysis was used to show that amplification and concomitant overexpression of the ABCC3 gene is most likely responsible for conferring resistance to paclitaxel and MMAE. It is also shown that this amplicon is present in primary breast tumors and that it is common in HER2 amplified and luminal tumors but not in basal-like cells (FIGS. 6 and 9).

Accordingly, one aspect of the invention provides for methods for determining whether a cancer will be resistant to treatment with an anti-mitotic agent. In one embodiment, the method comprises detecting whether the ABCC3 gene is amplified in a sample of the cancer cells. Amplification of the ABCC3 gene indicates that the cancer is resistant to the anti-mitotic agent. Detection of ABCC3 gene amplification can be performed by any method known in the art. In one embodiment, ABCC3 gene amplification is performed by detecting whether the copy number of the ABCC3 gene is increased in a sample of the cancer cells. In some embodiments, a gene is amplified if the copy number is at least 3, or alternatively at least 4, or alternatively at least 5, or alternatively at least 7, or alternatively at least 9, or alternatively at least 10.

Gene copy number can be determined by any means known in the art, for example, by fluorescence in situ hybridization (FISH), Southern Blot, immunohistochemisty (IHC), polymerase chain reaction (PCR), quantitative PCR (qPCR), quantitative real-time PCR (qRT-PCR), comparative genomic hybridization, microarray based comparative genomic hybridization, or ligase chain reaction (LCR). See for example, Avison, M., *Measuring Gene Expression*, New York: Taylor & Francis Group, 2007, Allison, D. B., et al, ed. *DNA Microarrays and Related Genomics Techniques: Design, Analysis, and Interpretation of Experiments* (*Biostatistics*), Boca Raton: Chapman & Hill/CRC, 2006; Hayat M. A., ed., *Handbook of Immunohistochemistry and in Situ Hybridization of Human Carcinomas*, Burlington: Elsevier Academic Press, 2004.

In a further embodiment, the method of determining whether a cancer will be resistant to an anti-mitotic agent comprises detecting whether the ABCC3 gene is overexpressed in a sample of the cancer cells. Overexpression of the ABCC3 gene indicates that the cancer is resistant to the anti-mitotic agent. Detection of ABCC3 overexpression can be performed by any method known in the art. In one embodiment, ABCC3 gene overexpression is detected by determining the level of mRNA transcription from the ABCC3 gene. Levels of mRNA transcription may be determined, either quantitatively or qualitatively, by various methods known to those skilled in the art. Levels of mRNA transcription may also be determined directly or indirectly by detecting levels of cDNA generated from the mRNA. Exemplary methods for determining levels of mRNA transcription include, but are not limited to, PCR, real-time quantitative RT-PCR and hybridization-based assays, including microarray-based assays and filter-based assays such as Northern blots. In certain embodiments, the ABCC3 gene is overexpressed if the level of mRNA transcription is at least a 3-, 5-, 7-, 10-, 15-, 20-, 25-, 30-, 35-, 40-, 45-, or 50-fold increase in mRNA transcription as compared to an appropriate control sample.

In other embodiments, expression of the ABCC3 gene is detected by determining the level of ABCC3 polypeptide expression. Levels of ABCC3 polypeptide may be determined, either qualitatively or quantatively, by certain methods known to those skilled in the art, including antibody-based detection methods. In one embodiment, detecting expression of the ABCC3 gene in a test cancer sample comprises contacting the test cancer sample with an anti-ABCC3 antibody and determining the level of expression (either quantitatively or qualitatively) of ABCC3 in the test cancer sample by detecting binding of the anti-ABCC3 antibody to ABCC3 polypeptide. In certain embodiments, binding of an anti-ABCC3 antibody to ABCC3 polypeptide may be detected by various methods known to those skilled in the art including, but not limited to, immunohistochemistry, fluorescence activated cell sorting, Western blot, radioimmunoassay, ELISA, and the like. In certain embodiments, overexpression of ABCC3 means at least a 3-, 5-, 7-, 10-, 15-, 20-, 25-, 30-, 35-, 40-, 45-, or 50-fold increase in ABCC3 polypeptide levels as compared to an appropriate control sample.

A sample of the cancer cells, or test cancer sample, preferably comprises cells taken directly from the cancer tumor, but the test cancer sample can also be comprised of metastatic cancer cells, circulating tumor cells, or any suitable sample of cells that identify the amplification or expression status of the ABCC3 gene in the cancer. Examples of cancers that can tested include breast cancer, ovarian cancer, colorectal cancer, prostate cancer, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, liver cancer, bladder cancer, hepatoma, colon cancer, rectal cancer, endometrial or uterine carcinoma, salivary gland carcinoma, kidney cancer, liver cancer, vulval cancer, thyroid cancer, hepatic carcinoma, leukemia and other lymphoproliferative disorders, various types of head and neck cancer, and any other cancer that is suitable for treatment using an anti-mitotic agent.

Appropriate controls for determining overexpression of ABCC3 in the cancer can be generated, for example, by determining the expression level of ABCC3 in control samples of cells or tissues that express a normal level of ABCC3 and comparing the level of expression of ABCC3 in the cancer to the level of expression of ABCC3 in the control sample. Alternatively, a control can be generated by determining the expression of a housekeeping gene (such as an actin family member) in the same test cancer sample used to determine ABCC3 overexpression, or in a sample from the same cancer to be tested for ABCC3 overexpression. The housekeeping gene acts as a comparative control on which to determine overexpression of the ABCC3 gene.

Detection of ABCC3 amplification and/or overexpression accordingly allows for patients suffering from cancer to select an appropriate method of therapy most likely to successfully treat their cancer.

Accordingly, it is one aspect of this invention to provide methods for selecting a cancer patient for anti-mitotic agent-based chemotherapy. Those patients whose cancer shows amplification or overexpression of ABCC3 could use that information to decide with their physician if they should pursue a therapeutic alternative to anti-mitotic therapy. In one embodiment, the method comprises detecting whether the ABCC3 gene is amplified in a test cancer sample from the patient, and selecting the patient for anti-mitotic drug-based chemotherapy if amplification of the ABCC3 gene is not detected in the test cancer sample. In another embodiment, the method comprises detecting whether the ABCC3 gene is overexpressed in a test cancer sample from the patient, and selecting the patient for anti-mitotic drug-based chemotherapy if overexpression of the ABCC3 gene is not detected in the test cancer sample.

In one embodiment, the patient is a breast cancer patient. In a further embodiment, the patient has Her2 positive breast cancer. Expression or amplification of HER2 in breast cancer (Her2 positive breast cancer) is associated with enhanced clinical benefit from the addition of the anti-mitotic agent paclitaxel after adjuvant treatment with doxorubicin compared to patients with HER2-negative, estrogen-receptor-positive, node-positive breast cancer (52). However, a significant fraction of women with HER2-positive tumors fail to show a survival benefit from this treatment (52), suggesting that paclitaxel resistance mechanisms are present in a proportion of HER2 positive breast tumors. This resistance to anti-mitotic agents is of particular concern for therapeutic regimes utilizing anti-Her2 antibodies conjugated to anti-mitotic agents, such as, for example, trastuzumab-DM1 antibody conjugates. As illustrated in the Examples, overexpression of ABCC3 is associated with resistance to treatment with trastuzumab-anti-mitotic agent conjugates. Conversely, knockdown of the ABCC3 gene with siRNA increases sensitivity of the cells to treatment with trastuzumab-anti-mitotic agent conjugates. Accordingly, the invention provides for methods of selecting a Her2-positive breast cancer patient for treatment with anti-Her2 antibody-anti-mitotic agent conjugate. In one embodiment, the method comprises detecting whether the ABCC3 gene is amplified in a test breast cancer sample from the patient, and selecting the patient for treatment with an anti-Her2 antibody-anti-mitotic agent conjugate if amplification of the ABCC3 gene is not detected in the test breast cancer sample. In another embodiment, the method comprises detecting whether the ABCC3 gene is overexpressed in a test breast cancer sample from the patient, and selecting the patient for treatment with anti-Her2 antibody-anti-mitotic agent conjugate if overexpression of the ABCC3 gene is not detected in the test breast cancer sample. In some embodiments, the method involves determining whether the patient has Her2 positive breast cancer if this information is not already known, thus determining suitability for treatment with anti-Her2 antibody therapy. In some embodiments, the anti-Her2 antibody-anti-mitotic agent conjugate is a trastuzumab-anti-mitotic agent conjugate such as trastuzumab-DM1 or trastuzumab-MMAE.

The invention also provides methods of treating cancer patients based on the ABCC3 amplification status of their cancer. In one embodiment, the method comprises detecting whether the ABCC3 gene is amplified in a test cancer sample from the patient and administering to the patient a therapeutically effective amount of an anti-mitotic drug-based chemotherapy if amplification of the ABCC3 gene is not detected in the test cancer sample. In another embodiment, the method comprises detecting whether the ABCC3 gene is overexpressed in a test cancer sample from the patient and administering to the patient a therapeutically effective amount of an anti-mitotic drug-based chemotherapy if overexpression of the ABCC3 gene is not detected in the test cancer sample. In one embodiment, the patient has Her2 positive breast cancer and is administered an anti-Her2 antibody-anti-mitotic agent conjugate if amplification or overexpression of the ABCC3 gene is not detected in the test cancer sample. In some embodiments, the anti-Her2 antibody-anti-mitotic agent conjugate is a trastuzumab-anti-mitotic agent conjugate such as trastuzumab-DM1 or trastuzumab-MMAE.

In yet another embodiment, a patient is selected for anti-mitotic drug-based chemotherapy based on absence of ABCC3 amplification or overexpression in their cancer and administered a therapeutically effective amount of an anti-mitotic drug-based chemotherapy. In one embodiment, the selected patient has Her2 positive breast cancer and is administered an anti-Her2 antibody-anti-mitotic agent conjugate. In some embodiments, the anti-Her2 antibody-anti-mitotic agent conjugate is a trastuzumab-anti-mitotic agent conjugate such as trastuzumab-DM1 or trastuzumab-MMAE.

Another aspect of the invention provides for a method of identifying gene amplification variations that are associated with altered drug sensitivity. Most in vitro profiling efforts directed at understanding drug resistance to date have focused on gene expression analyses. The present invention describes the identification of DNA copy number alterations that are associated with altered drug sensitivity through analyses of high density SNP array profiles (Affymetrix). Recent studies have shown that high density single nucleotide polymorphism (SNP) arrays, in addition to their intended application in genotyping, can be used to detect genome wide DNA copy number changes and loss of heterozygosity in human cancers (17). These arrays have been shown to have applications in the identification of tumor suppressor and oncogene loci by pinpointing recurrently deleted or amplified chromosomal regions (18).

The data presented herein shows that the arrays can be used to identify amplified regions harboring genes that may modulate the activity of therapeutic drugs. A key advantage of this approach is that gene amplification events are relatively stable and can ultimately be assayed on archival samples from clinical trials. One particularly appropriate assay to detect gene amplification events in the archival samples is fluorescence in situ hybridization (FISH). FISH assays are already part of routine clinical practice in the diagnosis of HER2 positive MBC (50) and are currently being evaluated as diagnostic tests to detect EGFR amplification as a possible biomarker of response to Tarceva or Erbitux (51).

Still another aspect of the invention provides for methods of determining appropriate levels of dosing of an anti-mitotic agent for those patients whose cancers comprise amplification and/or overexpression of ABCC3. In one embodiment, the method comprises determining whether ABCC3 is amplified and/or overexpressed in a test cancer sample of a patient and administering to the patient an increased dose of anti-mitotic agent if ABCC3 is amplified or overexpressed. The dose of anti-mitotic agent is increased to an amount wherein the cancer shows a response to treatment with an anti-mitotic agent. In some embodiments, the dose of anti-mitotic agent administered to the patient is at least 1.2 times, or alternatively at least 1.3 times, or alternatively at least 1.5 times, or alternatively at least 2 times, or alternatively at least 2.5 times, or alternatively at least 3 times, or alternatively at least 5 times, or alternatively at least 10 times, the amount administered to a patient whose cancer does not comprise ABCC3 amplification and/or overexpression.

Yet another aspect of the invention provides for methods of reducing resistance of a cancer cell to an anti-mitotic agent comprising contacting the cancer cell with an antagonist of ABCC3. In some embodiments, the ABCC3 antagonist serves to prevent amplification and/or overexpression of ABCC3 and decreases the drug resistance conferred by the amplification and/or overexpression. In other embodiments, the ABCC3 antagonists serve to inhibit ABCC3 activity. Antagonists that are useful in the methods include ABCC3 antibodies, RNA interference (RNAi) based ABCC3 antagonists, especially antisense RNA, miRNA, siRNA, and shRNAs, ABCC3 polypeptide binding oligopeptides, and ABCC3 binding organic molecules.

A further aspect of the invention provides for a combination therapy for treating a patient with a cancer that is resistant to anti-mitotic agents comprising administering to the patient an antagonist of ABCC3 and an anti-mitotic agent. In some embodiments, the antagonist is selected from the group consisting of an ABCC3 antibody and an siRNA that binds to ABCC3. In some embodiments the anti-mitotic agent is selected from the group consisting of taxanes, maytansinoids, and auristatins, and analogs and deriviatives thereof. In some embodiments, the anti-mitotic agent is conjugated to an antibody such as a maytansinoid-anti-Her2 antibody conjugate, for example, trastuzumab-DM1. In one embodiment, the combination therapy comprises treatment with an siRNA that binds to ABCC3 and trastuzumab-DM1.

Such combination therapies noted above encompass combined administration (where two or more therapeutic agents are included in the same or separate formulations), and separate administration, in which case, administration of an ABCC3 antagonist can occur prior to, simultaneously, and/ or following, administration of the anti-mitotic agent.

In one embodiment, the ABCC3 antagonist is an anti-ABCC polypeptide antibody. Exemplary antibodies include polyclonal, monoclonal, humanized, bispecific, and heteroconjugate antibodies.

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. In certain embodiments, the animals used to raise antibodies may be transgenic animals. In certain such embodiments, the animals may be engineered such that they exhibit a complete absence of a polynucleotide encoding ABCC3, such that they have no ABCC3 expression (referred to as "knockout" animals). Methods of generating such animals are well-known in the art, see, e.g., Snouwaert et al., Science 257: 1083, 1992; Lowell et al., Nature 366:740-42, 1993; Capecchi, M. R., Science 244: 1288-1292, 1989. Raising antibodies to a particular protein or peptide in a knockout animal for that protein or peptide may be advantageous because anti-self reactions in the animal that may reduce production and/or yields of the antibody should not occur, as is well known in the art.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256:495 (1975), or may be made by recombinant DNA methods (U.S. Pat. No. 4,816,567).

The anti-ABCC3 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')₂ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-ABCC3 polypeptide antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno. 7:33 (1993); U.S. Pat. Nos. 5,545,806, 5,569,825, 5,591,669 (all of GenPharm); 5,545,807; and WO 97/17852.

Alternatively, phage display technology (McCafferty et al., Nature 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

Another potential ABCC3 antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature ABCC3 polypeptide herein, can be used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the ABCC3 polypeptide. The antisense RNA oligonucleotide hybridizes to the mRNA in vivo and blocks translation of the mRNA molecule into the ABCC3 polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the ABCC3 polypeptide. When antisense DNA is used, oligodeoxyribonucleotides derived from the translation-initiation site, e.g., between about −10 and +10 positions of the target gene nucleotide sequence, are preferred.

Small interfering RNAs (siRNAs) are double stranded RNA molecules generally less than 30 nucleotides in length that reduce expression of a target gene. siRNAs have proven useful as a tool in studies of modulating gene expression where traditional antagonists such as small molecules or antibodies have failed. (Shi Y., Trends in Genetics 19(1):9-12 (2003)). In vitro synthesized, double stranded RNAs that are 21 to 23 nucleotides in length can act as interfering RNAs (iRNAs) and can specifically inhibit gene expression (Fire A., Trends in Genetics 391; 806-810 (1999)). These iRNAs act by mediating degradation of their target RNAs. Since they are under 30 nucleotides in length, however they do not trigger a cell antiviral defense mechanism. In some embodiments of the invention, the siRNA has at least about 90%, 91%, 92%, 93%, 94%, 95%, 96%, 97%, 98%, 99%, or 100% nucleic acid sequence identity with a portion of the coding sequence of the ABCC3 encoding polynucleotide or its complement.

ABCC3 polypeptide binding oligopeptides of the invention are oligopeptides that bind, preferably specifically, to an ABCC3 polypeptide as described herein. ABCC3 polypeptide binding oligopeptides may be chemically synthesized using known oligopeptide synthesis methodologies or may be prepared and purified using recombinant technology. ABCC3 polypeptide binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a ABCC3 polypeptide as described herein. ABCC3 polypeptide binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA*, 87:6378) or protein (Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

ABCC3 polypeptide binding small molecules are preferably organic molecules other than oligopeptides or antibodies as defined herein that bind, preferably specifically, to an ABCC3 polypeptide as described herein. ABCC3 polypeptide binding organic small molecules may be identified and chemically synthesized using known methodology (see, e.g., PCT Publication Nos. WO00/00823 and WO00/39585). ABCC3 polypeptide binding organic small molecules are usually less than about 2000 daltons in size, alternatively less than about 1500, 750, 500, 250 or 200 daltons in size, wherein such organic small molecules that are capable of binding, preferably specifically, to a ABCC3 polypeptide as described herein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). ABCC3 polypeptide binding organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

Pharmaceutical formulations comprising any of the above agents are prepared for storage by mixing the antibody or immunoconjugate having the desired degree of purity with optional physiologically acceptable carriers, excipients or stabilizers (*Remington's Pharmaceutical Sciences* 16th edition, Osol, A. Ed. (1980)) in the form of aqueous solutions or lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride); phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutical formulations to be used for in vivo administration are generally sterile. This is readily accomplished by filtration through sterile filtration membranes.

An agent may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the agent of interest, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated agents remain in the body for a long time, they may denature or aggregate as a result of exposure to moisture at 37° C., resulting in a loss of biological activity and, for antibodies, possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Anti-Mitotic Agents

An anti-mitotic agent is any compound that inhibits, prevents, or otherwise disrupts mitosis. Specific examples of anti-mitotic agents include, but are not limited to, taxanes, such as paclitaxel and docetaxel; maytansinoids, including maytansinol and maytansinol analogues modified in the aromatic ring or at other positions of the maytansinol molecule, such as various maytansinol esters, and DM1 and DM4; dolastatin 10, dolastatin 15, and auristatins, such as monomethyl auristatin E (MMAE) and monomethyl auristatin F (MMAF); vinca alkoloids, such as vinblastine and vincristine; and analogs and deriviatives thereof.

The taxanes are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

Maytansinoids are tubulin-binding agents that are potent anti-mitotics, causing cells to arrest in the G2/M phase of the cell cycle and ultimately leading to cell death. Maytansinoids are derivatives of the maytansine, a compound first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, and Kawai et al (1984) Chem. Pharm. Bull. 3441-3451).

The auristatins are analogs of dolastatin 10 (a pentapeptide natural product), including monomethyl auristatin E (MMAE) and monomethyl auristatin F (MMAF). Molecules in this family inhibit tubulin polymerization. In general, the activities are 100-1,000 times more potent than doxorubicin. (Pettit, G. R., *The dolastatins*. Progress in the Chemistry of Organic Natural Products 70, 1-79, 1997).

The anti-mitotic agent is optionally conjugated to an antibody.

There are many linking groups known in the art for making antibody-agent conjugates. Antibody-maytansinoid conjugates have been widely described in the literature. See, for example, U.S. Pat. No. 5,208,020 or EP Patent 0 425 235 B1, and Chari et al., Cancer Research 52:127-131 (1992). The linking groups useful for making antibody-agent conjugates include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid, or other anti-mitotic agent, may be made using a variety of bifunctional protein coupling agents such as N-succinimidyl-3-(2- pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In one embodiment, the linkage is formed at the C-3 position of maytansinol or a maytansinol analogue.

Examples of anti-mitotic-antibody conjugates include, but are not limited to, trastuzumab-DM1 (Genentech/ImmunoGen, described in U.S. Pat. No. 7,097,840, incorporated by reference in its entirety herein), Trastuzumab-auristatin (Genentech/Seattle Genetics), Cantuzumab mertansine (huC242-DM1, SB-408075) (ImmunoGen), BB-10901 (huN90'-DM1) (ImmunoGen), MLN2704(DM1) (Millennium Pharmaceuticals), Bivatuzumab mertansine (DM1) (Boehringer Ingelheim), huMy9-6-DM4 (AVE9633) (Sanofi-aventisc), huC242-DM4 (ImmunoGen), SGN-35 (Monomethyl auristatin) (Seattle Genetics), SGN-75 (Monomethyl auristatin) (Seattle Genetics), and CR011-vcMMAE (Curagen/Seattle Genetics). Lambert, J. M., et al, Current Opinion in Pharmacology, 5:543-549 (2005). See also US20050276812, WO2004110498, Wul, A. M., and Senter, P. D., Nature Biotech 23: 1137-1146 (2005).

Trastuzumab-MCC-DM1 (T-DM1) (CAS Reg. No. 139504-50-0) has the structure:

where Tr is trastuzumab, linked through linker moiety MCC, to the maytansinoid drug moiety, DM1 (U.S. Pat. Nos. 5,208,020; 6,441,163). The drug to antibody ratio or drug loading is represented by p in the above structure of trastuzumab-MCC-DM1, and ranges in integer values from 1 to about 8. The drug loading value p is 1 to 8. Trastuzumab-MCC-DM1 includes all mixtures of variously loaded and attached antibody-drug conjugates where 1, 2, 3, 4, 5, 6, 7, and 8 drug moieties are covalently attached to the antibody trastuzumab (U.S. Pat. No. 7,097,840; US 2005/0276812; US 2005/0166993). Trastuzumab is an antibody that has antigen binding residues of, or derived from, the murine 4D5 antibody (ATCC CRL 10463, deposited with American Type Culture Collection, 12301 Parklawn Drive, Rockville, Md. 20852 under the Budapest Treaty on May 24, 1990). Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337.

Trastuzumab-DM1 (or T-DM1) has been shown to be efficacious in trastuzumab-sensitive and trastuzumab-insensitive models of HER2-overexpressing cancer. Clinical studies are currently under way to assess the safety and efficacy of T-DM1 in patients with HER2-overexpressing breast cancer.

EXAMPLES

Example 1

Techniques and Assays

Cell Lines and Viability Experiments

Breast cancer cell lines AU565, BT-474, BT-549, CAMA-1, DU4475, HCC1143, HCC1419, HCC1428, HCC2218, HCC70, Hs578T, KPL-1, MCF-7, MDA-MB-231, MDA-MB-435S, MDA-MB-436, MDA-MB-453, MDA-MB-468, T-47D, UACC-812, ZR-75-1 and ZR-75-30 were obtained from American Type Culture Collection (ATCC, Manassas, Va.). The cell lines CAL-120, CAL-148, CAL-51, CAL-85-1, EFM-19, EFM-192A, EVSA-T, and MT-3 were obtained

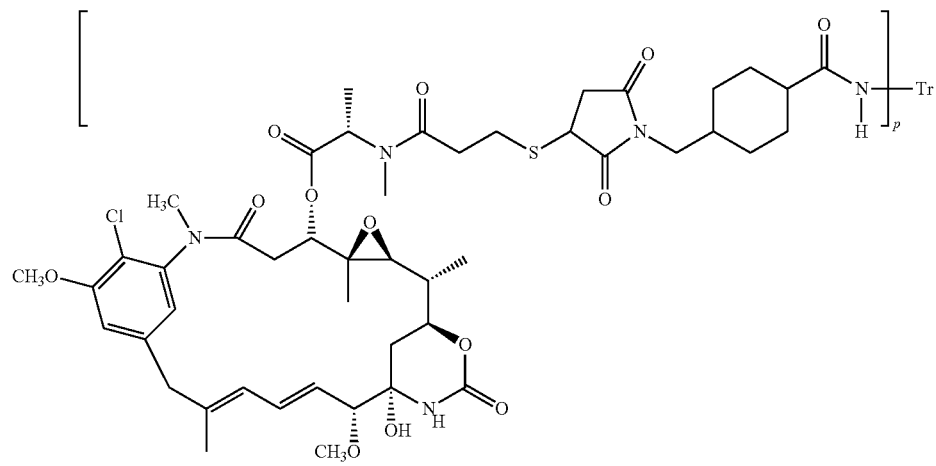

from the Deutsche Sammlung von Mikroorganismen and Zellkulturen GmbH (DSMZ, Braunschweig, Germany). All cell lines were maintained in RPMI 1640 or DMEM supplemented with 10% fetal bovine serum (Sigma, St. Louis, Mo.), non-essential amino acids and 2 mmol/L L-glutamine. Though annotated as breast lines, MDA-MB-4355 may actually be of melanoma origin and MT-3 of colorectal origin based on molecular and genetic criteria (19, 20). These findings do not impact the conclusions of this study.

For MMAE and paclitaxel IC50 determination, cells were plated in quadruplicate at a density of 3000 cells per well in 384-well plates in normal growth medium and allowed to adhere overnight. Paclitaxel (Sigma) or MMAE (Seattle Genetics, Seattle, Wash.) were added in 10 concentrations based on a three-fold dilution series (1 µmol/L maximal paclitaxel or 0.1 µmol/L maximal for MMAE).

Cell viability was measured 72 hours later using the Celltiter-Glo Luminescent Cell Viability Assay (Promega, Madison, Wis.). The concentration of drug resulting in the 50% inhibition of cell viability (IC50) was calculated from a four-parameter curve analysis (XLfit, IDBS software) and was determined from a minimum of three experiments. Cell lines that did not show 50% reduction in cell viability in response to drug treatment in the majority of experiments conducted were considered to not have reached an IC50 by definition and are listed as having an IC50 of >100 nM (MMAE) or >1000 nM (paclitaxel). FIG. 6 provides examples of representative cell viability experiments for six cell lines. Cell lines EFM192A, NDAMB361, and BT474 were classified as resistant to each agent in the bioinformatic analysis. AU565, EFM19, and MDAMB468 were classified as sensitive. IC50 values from fitted curves are shown in the charts to the right of each graph.

Figure 5A:
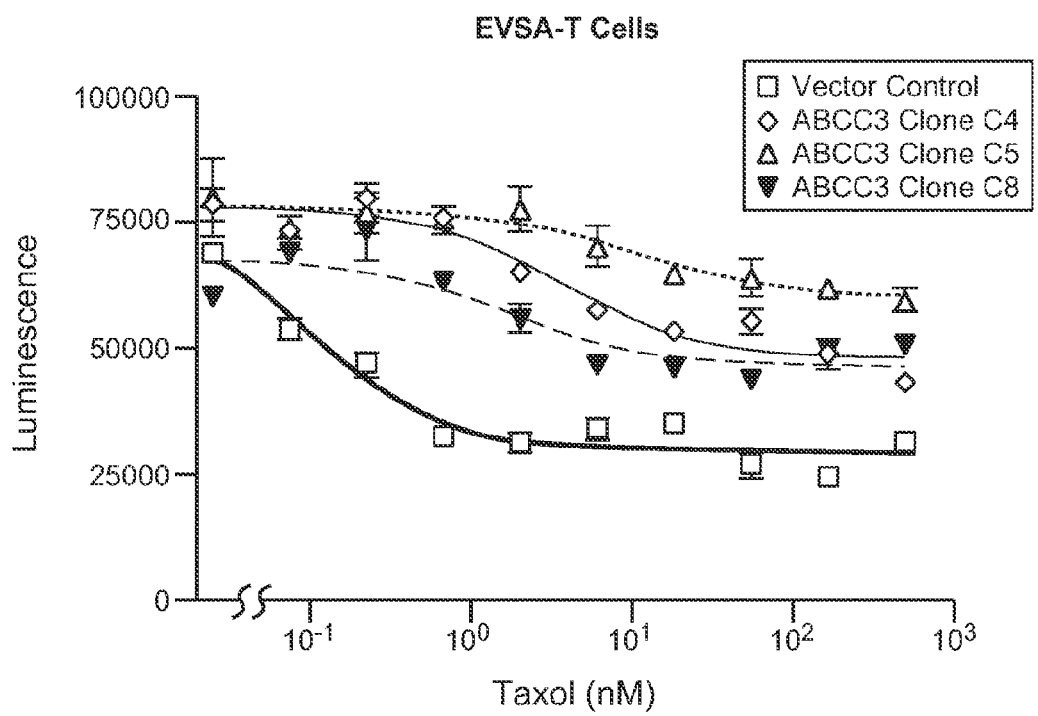
FIG. 5 shows that stable overexpression of ABCC3 results in vitro resistance to paclitaxel and MMAE. Stable cell lines derived from single cell clones that overexpress ABCC3 from the CMV promoter or a control line with empty vector were assayed for growth inhibitory effects of paclitaxel (FIG. 5a) or MMAE (FIG. 5b).
Figure 5B:
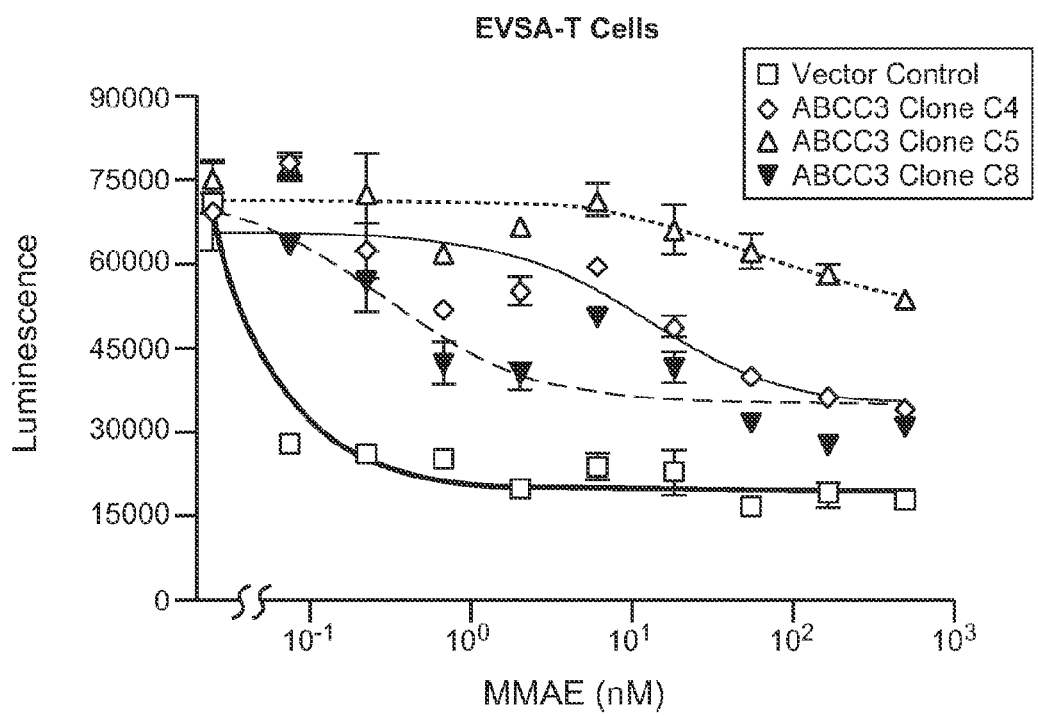

For ABCC3-overexpressing clones of the EVSA-T cell line that did not achieve IC50, we calculated the half-maximal effect concentration, or EC50, in GraphPad Prism software (GraphPad Software, Inc). The control cell line in FIG. 5 is in fact a clone of EVSA-T derived after transfection with an empty vector and in the particular experiment shown achieved an IC50.

Breast Tumor Samples

Primary breast tumors from 145 independent breast cancer patients were utilized to make genomic DNA for Agilent Array CGH analysis (21). All the tumors were fresh frozen and found to have greater than 70% tumor content, and all were classified as infiltrating ductal carcinoma. ABCC3 FISH studies were conducted on 61 additional independent primary breast tumor samples from the Genentech tumor bank.

Gene Expression Microarray Studies

Gene expression analysis of breast cancer cell lines was carried out on RNA extracted from sub-confluent cell cultures using Qiagen RNAeasy kits. RNA quality was verified by running samples on an Agilent Bioanalyzer 2100 and samples of sufficient quality were profiled on Affymetrix HGU133Plus_2.0 chips (Santa Clara, Calif.). Preparation of complementary RNA, array hybridizations, scanning and subsequent array image data analysis were done using the manufacturer's specified protocol.

For overall unsupervised hierarchical clustering analysis of breast cancer cell lines, gene expression data were filtered to remove probe sets that showed little variation across the cell lines. Briefly, probes that did not show at least a five fold variation across the samples (max/min >10) and an absolute intensity difference of at least 250 (max-min >250) were excluded from hierarchical clustering analysis. Data preprocessing involved log transforming and median centering gene expression values, after which average linkage clustering was carried out using Cluster and TreeView software (22).

SNP Array and Agilent aCGH Copy Number Studies

Cell line copy number analysis was carried out on genomic DNA extracted from sub-confluent cell cultures using Qiagen DNAeasy kits. For each cell line 500 ng of genomic DNA was hybridized to Genechip 100K mapping arrays (Affymetrix, Inc., Santa Clara, Calif.) according to the manufacturer's instructions. These arrays contain probe sets for more than 116,000 SNP loci derived from all human chromosomes (except the Y chromosome), with a mean marker distance of 26 kb (23). SNP calls and signal quantification were obtained with Gene Chip Operating System. Agilent Human Genome 244A CGH microarrays and Agilent feature extraction software were run according to the manufacturer's instructions and Genome-smoothed analysis DNA copy number (GSA_CN) was calculated based on the hybridization intensity (the sum of both allele intensities) for each SNP probe with the Affymetrix Chromosome Copy Number Analysis Tool 3.0 (CNAT 3.0). Copy number data were segmented with the GLAD segmentation algorithm (24).

Associations between GSA_CN copy number and drug sensitivity were identified with Matlab software (The MathWorks, Inc. Natick, Mass., USA) using a version of the maxT procedure (26). For each drug, a test statistic was calculated for each SNP reflecting the difference between log-transformed copy number in sensitive and resistant cell lines. The statistic was calculated as the absolute value of a standard t statistic (two sample, unequal variance), except that it was set to zero for those SNPs with less than 1.75-fold difference in mean copy number between sensitive and resistant classes. Then the null distribution of maximum test statistics across all SNPs was estimated in 10,000 random permutations of the sensitivity labels. The p-value for each SNP was calculated as the fraction of permutations in which the maximum test statistic was greater than or equal to the observed statistic for that SNP. The resulting p-values control the family-wise error rate and take into account the number of SNPs tested.

HER2 copy number determination by Quantitative RT PCR

Quantitative PCR was performed using ABI Prism 7700 Sequence Detection System (Applied Biosystems, Foster City, Calif.) on genomic DNA prepared as described above. qRT-PCR was performed using primers CACTGTCTG-CACCTTGCTTTG (SEQ ID NO: 1) and GCTCTGCAGC-TATTGAAAGAACAA (SEQ ID NO: 2) for Her 2 and AAAGCCGCTCAACTACATGG (SEQ ID NO:3) and TGCTTTGAATGCGTCCCAGAG (SEQ ID NO: 4) for Line-1 repetitive elements. Line-1 is a repetitive element with similar copy numbers per haploid genome between human normal and neoplastic cells (27). Quantification was based on standard curves from a serial dilution of human normal genomic DNA. The relative target copy number level was also normalized to normal human genomic DNA as calibrator. Copy number change of target gene relative to the Line-1 and the calibrator were determined using the formula E−[(CPtarget−Cpref)control−(CPtarget−Cpref)test] as described by Kindich et al (28). Conditions for quantitative PCR reaction were as described in the Invitrogen Platinum® SYBR® Green qPCR SuperMix-UDG w/ROX package insert (catalog number 11744-500).

Fluorescence In Situ Hybridization (FISH) Analysis
Probes

A bacterial artificial chromosome (BAC) contig comprising of 2 overlapping clones, CTD-2605A1 and CTD-3006C13, covering the entire ABCC3 loci and adjoining areas (based on the USCS Genome Browser March 2006 assembly) were used as a probe for the FISH experiments. Commercially available probes for HER2/CEP17 (Pathvysion, Vysis/Abbott Laboratories, Des Plaines, Ill.) and CEP17 (Vysis/Abbott Laboratories, Des Plaines, Ill.) were also used for the FISH experiments.

FISH Analysis

Cell lines were prepared for cytogenetic analysis by incubation with 0.1 μg/mL Colcemid (Invitrogen) for 2-3 h, followed by osmotic swelling in KCl (0.075 M) and fixation in methanol: acetic acid (3:1), as previously described (29). DNA from the BAC clones was extracted by standard methods.

The extracted BAC DNA was directly labeled with Spectrum Orange, Spectrum Green, (Vysis/Abbott Laboratories, Des Plaines, Ill.) or diethylaminocoumarin (DEAC) (Invitrogen) by nick translation using the Vysis Nick Translation Kit (Vysis/Abbott Laboratories) according to the manufacturer's instructions. FISH to normal human metaphases (Abbott Laboratories, Des Plaines, Ill.) confirmed the genomic location of the BAC clones. Approximately 300 ng of labeled probes were precipitated in excess Human Cot-1 DNA (Invitrogen) and sonicated salmon sperm DNA (Sigma) and resuspended in a 50% formamide, 10% dextran sulfate, and 2'SSC hybridization buffer (Vysis/Abbott Laboratories, Des Plaines, Ill.) for the FISH experiments. FISH on cytogenetic preparations and formalin fixed paraffin embedded (FFPE) tissue was performed as described previously (Pandita et al., 2004), with some modifications. After an overnight incubation at 56°-60° C., the slides were deparaffinized in 3 washes of CitroSolv for 5 min each, followed by two washes in alcohol. After air-drying, the slides were incubated in a 1M solution of NaSCN for 30 min at 80° C. and then were treated with pepsin prior to additional washes in water and a series of ethanol. Dried slides were then co-denatured (76° C. for 6 min) with the probe and were hybridized overnight at 37° C. (ThermoBrite; Vysis, Downers Grove, Ill.). Post-hybridization washes and counter-staining were done in a manner similar to those previously described. The slides were visualized using an Olympus BX61 microscope and analyzed using FISHView software (Applied Spectral Imaging, Vista Calif.). The copy number analysis and ratio of HER2/ABCC3 to CEP17 was performed as per the manufacturer's instructions.

Functional Validation Experiments

Figure 3:
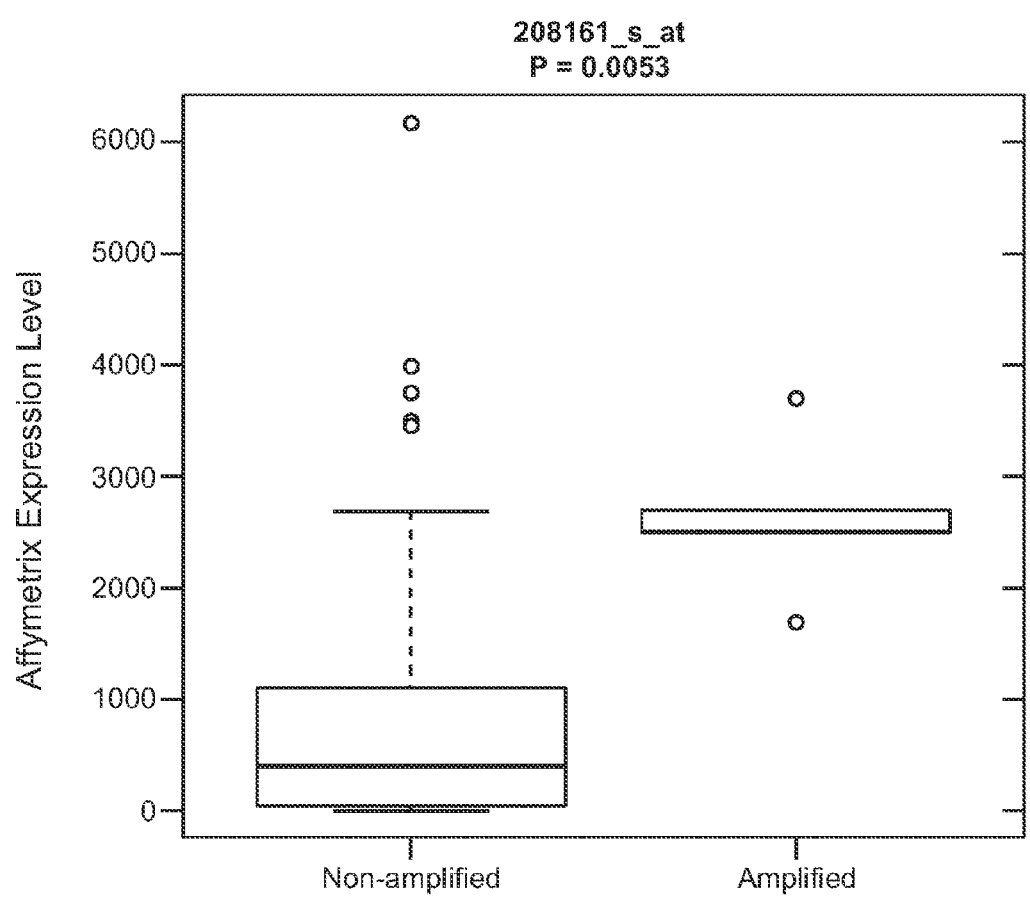
FIG. 3 shows that ABCC3 is overexpressed in cell lines with 17q21.3 amplification. Thirty-one cell lines were binned into amplified and non-amplified classes based on a copy number cutoff of 4 in the region. Box-and-whisker plots show expression of ABCC3 in each group. 208161_s_at was selected as the most variable Affymetrix expression probe set representing ABCC3. Other probe sets gave similar results. The central box represents the interquartile range, the line inside the box indicates the median, and the dotted vertical lines extend to the data points furthest from the median but within 1.5 times the interquartile range. Data points outside the dotted vertical lines are represented by individual circles.

High content screening assays were carried out on an Arrayscan VTI (Cellomics Inc, Pittsburgh, Pa.). Cells were transfected in 96 well format using siRNA "Smartpool" oligonucleotides purchased from Dharmacon Inc and Oligofectamine transfection reagents. To prioritize genes for functional studies, 2-sided Wilcoxon rank sum tests using the R programming language (http://www.r-project.org) were done to identify genes with a significant difference in gene expression in cell lines with more than 4 copies compared to those with less than 4 copies of the 17q21.3 amplicon. An example of differential expression for gene that emerged from this analysis, ABCC3 (p=0.0053) is shown in FIG. 3. This analysis combined with availability of reagents for RNAi experiments led to the selection of the following 24 genes for functional studies in the EFM-192A cell line: ABCC3, COL1A1, CROP, EAP, EPN3, FLJ13855, FLJ20920, HOXB7, LOC201191, ITGB3, KIAA0924, KPNB1, LOC400604, LOC81558, MGC11242, MGC15396, NDP52, PDK2, PHB, PP1R9B, SLC35B1, SPOP, TOB1, WNT3. Follow-up studies with ABCC3 siRNA were conducted in the additional cell lines ZR75-30, MDAMB-453 and HCC-1428. A non-targeting control (NTC) siRNA that does not show significant homology to any sequence in the human genome was used as a negative control in all RNAi experiments (as described in technical notes at www.dharmacon.com). After 48 hours or 72 hours incubation at 37 C, cells were fixed in 3.7% formaldehyde and permeabilized in 0.1% Triton X-100, followed by labeling with a 1:500 dilution of anti-phospho histone H3 (pH3, Upstate) and subsequent 1:250 dilution of Alexa-fluor 488 (Molecular probes) Goat anti-rabbit secondary antibody. Cells were counterstained with Hoechst-33258 to allow identification of nuclei and the percentage of cells positive for nuclear pH3 immunofluorescence, also known as the Mitotic Index (30), was then quantitated for at least 1000 cells per well using Cellomics Target Activation software. All experiments were repeated at least three times. qRT-PCR (5' primer GATTCCAGCCGCTTCAGTT (SEQ ID NO: 5), 3' primer CCTGGCTGTGCTCTACACCT (SEQ ID NO: 6) on a ABI 7900 was performed to confirm that the siRNA pool resulted in 90% knockdown of ABCC3 relative to a control siRNA.

For ABCC3 overexpression experiments a full length ABCC3 cDNA cloned in the CMV promoter containing vector pCMV5 (Invitrogen, Carlsbad, Calif.) was verified by sequencing the entire coding sequence. The construct was transfected into EVSA-T cells and stable clones were selected by growth in 1 mg/ml geneticin (Invitrogen Carlsbad, Calif.). Overexpression of ABCC3 in stable clones was confirmed by qRT-PCR on cDNA derived from lines containing pCMV5-ABCC3, pCMV5 vector alone, or the parental EVSA-T strain. All stable cell lines described in this report were determined in qRT-PCR experiments to express at least 25-35× more ABCC3 transcript than vector control lines or the parental cell line.

Example 2

Molecular Characterization of Cell Lines

Affymetrix gene expression profiling was performed on cDNA prepared from total mRNA and Affymetrix 100K SNP array profiling was done on DNA from 44 breast cancer cell lines. Unsupervised analysis with the 11,000 most differentially expressed genes across the cell line panel was used to classify the cell lines into luminal and basal-like subtypes based on gene expression (FIG. 11). Cell lines classified as luminal expressed high levels of estrogen receptor alpha (ER) and many of the target genes regulated by ER, including GATA3, HNF3A, IGF1R and XBP1. Cell lines classified as basal-like expressed high levels of some or all of the well described basal markers vimentin, caveolin, MFGE8 and the basal cytokeratins such as KRT5 (31). Because amplification of the HER2 oncogene clearly defines a separate disease subtype that is not apparent from overall gene expression classification in cell lines (14), the HER2 copy number was determined by qRT-PCR on genomic DNA and normalization to Line-1 repetitive elements for all cell lines (FIG. 11). Cell lines that show apparent copy number greater than four in these analyses are indicated as HER2 amplified in the Table shown in FIG. 11. The composite molecular subtype in FIG. 11 is a classification derived from both the overall gene expression results as well as the HER2 copy number analysis. These findings agree with previous reports (14) and suggest that this collection of breast cancer cell lines reflects to some degree the major transcriptional distinctions that define breast cancer subtypes and to some extent are representative as models of subtypes as luminal, basal-like, and HER2 amplified tumors. Genome wide patterns of copy number gain and loss in the cell line panel show that the breast cancer cell lines harbor most of the major copy number alterations (e.g. MYC, CCND1, HER2 gain and p16, PTEN loss) that have been described in tumors. Subtype specific differences have been described (32). A finding relevant to this study is that amplification at 17q21.3 is common in HER2 amplified and luminal cell lines but not in basal-like cell lines.

Example 3

Figure 1B:
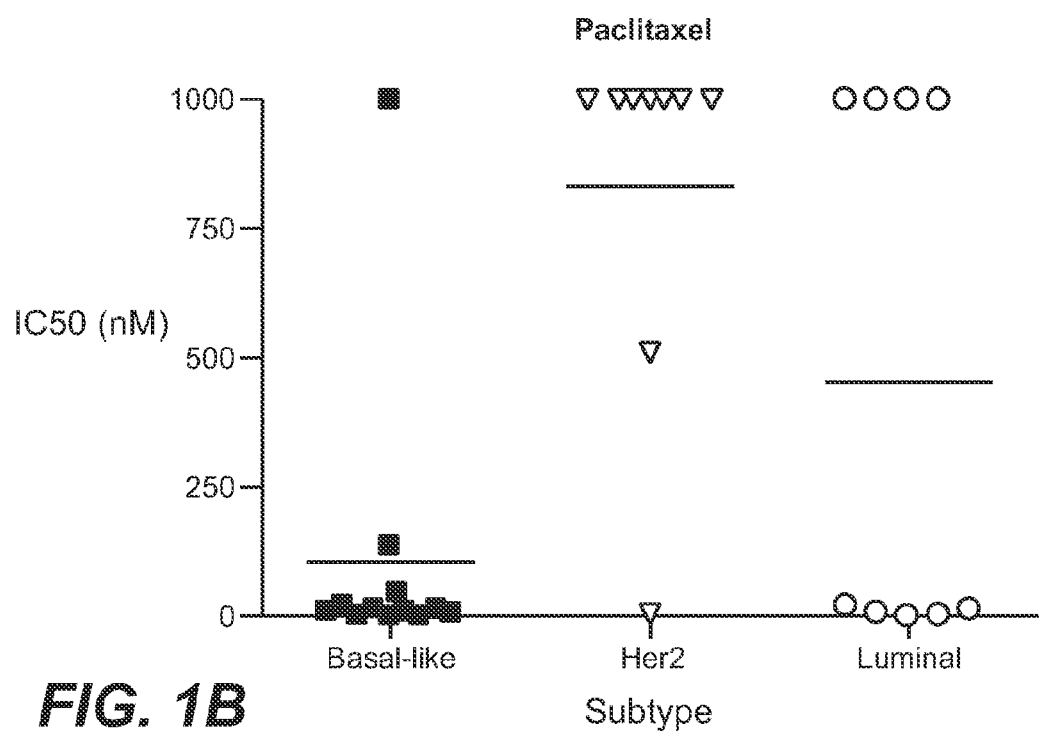
FIG. 1b illustrates an in vitro response of breast cancer cell lines to paclitaxel. On the x-axis, cell lines were classified into major molecular subtypes of breast cancer. The y-axis indicates the in vitro IC50 value, or concentration of drug that resulted in 50% inhibition of cell viability. Horizontal lines indicate mean sensitivity to each agent for cell lines of a given subtype.

In Vitro Sensitivity to Anti-mitotic Drugs 31 breast cancer cell lines were screened for in vitro sensitivity to paclitaxel and MMAE. FIG. 11 shows the IC50 value for each compound, defined as the concentration required for 50% inhibition of cell viability in a standard luciferin based viability assay in all of the cell lines. Notably there was significant correlation between the relative sensitivity to each agent across the panel of cell lines (Spearman rank order correlation coefficient, rs=0.55). In addition, FIG. 1 shows that cell lines with the basal-like gene expression signature had lower average IC50 values and were more sensitive to each agent than luminal or HER2 amplified cell lines as determined by Kruskal-Wallis rank sum test (P-value=0.002 for MMAE, P-value=0.005 for paclitaxel)

Example 4

Identification of Genomic Alterations that Correlate with In Vitro Sensitivity

Figure 2A:
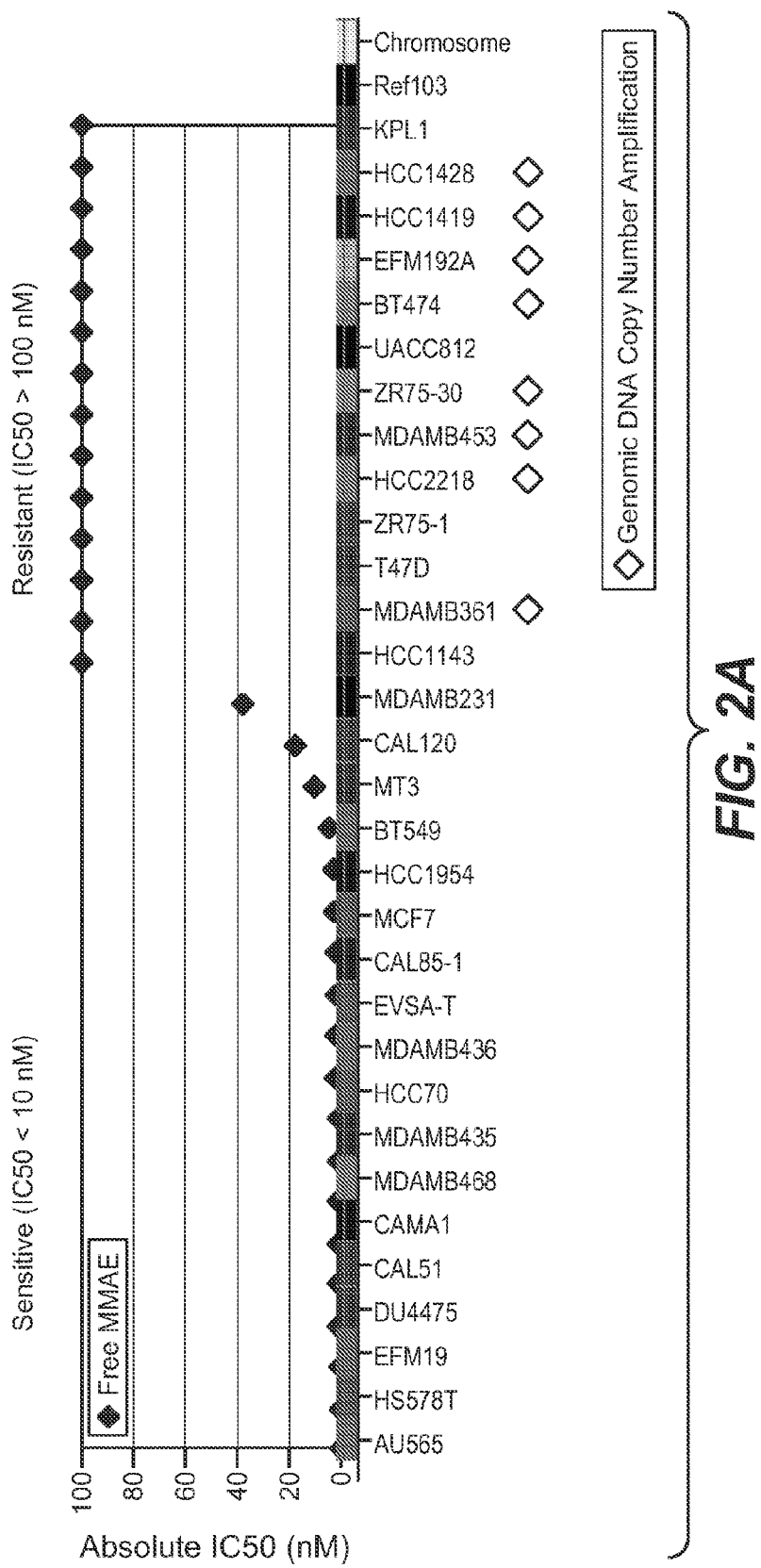
FIG. 2a shows that in vitro resistance to Paclitaxel is associated with amplification of the Chromosome 17q21 region.
Figure 2B:
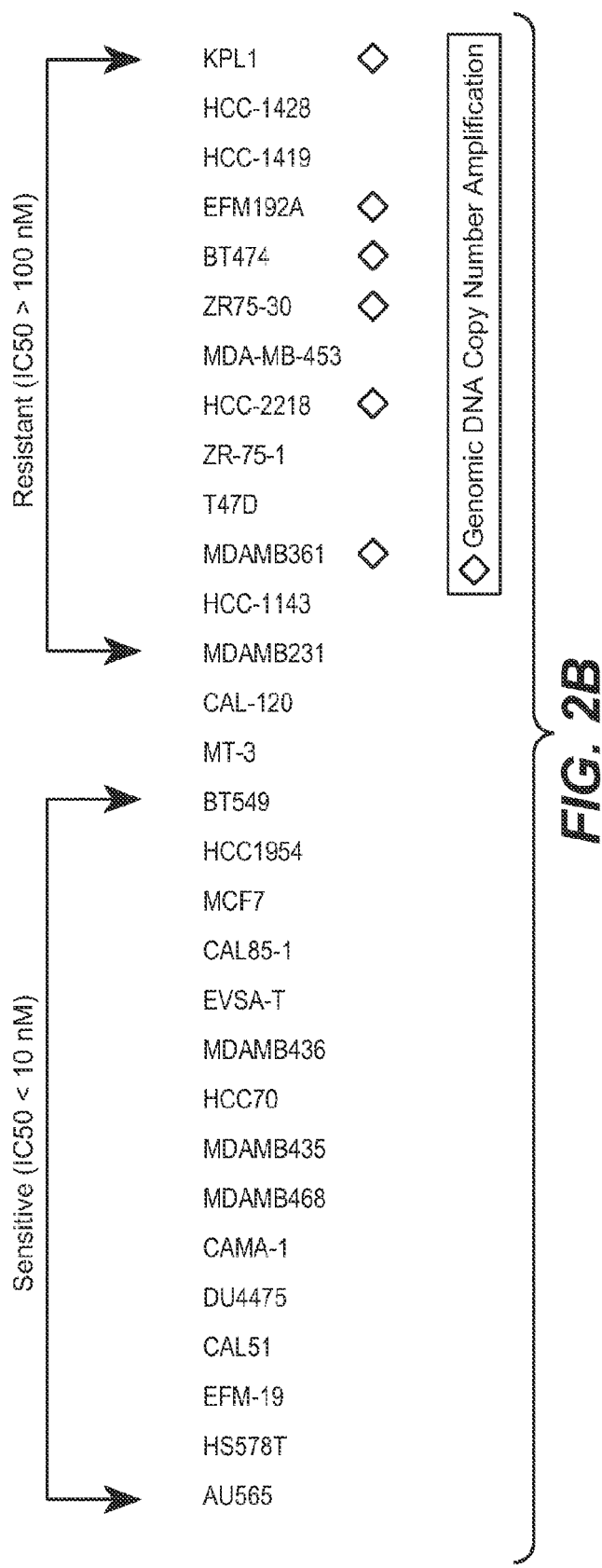
FIG. 2b shows that in vitro resistance to MMAE is associated with amplification of the Chromosome 17q21 region. Cell lines are shown in order of increasing agent sensitivity from left to right. The classifications (sensitive, intermediate, resistant) used for supervised analysis of SNP array data and identification of biomarkers of resistance are indicated at the top of the figure. Those cells lines with genomic DNA copy number amplification are indicated with a diamond.

The regions of chromosomal gain or loss that correlated with sensitivity to paclitaxel or MMAE were identified through supervised analysis of SNP array copy number data. First, cell lines were classified into either sensitive (IC50 <10 nM) or resistant (MMAE IC50 >100 nM, Paclitaxel IC50 >1000 nM) groups based on the sensitivity data. Then the maxT algorithm (26) was used to analyze data from approximately 115,000 SNPs and individual SNPs were identified where the mean copy number differed between sensitive and resistant classes with genome-wide significance. In the case of paclitaxel a group of SNPs on chromosome 17 starting at chromosome position 44,303,217 and ending at position 44,724,301 (17q21.21 to 17q21.23) showed statistically significant copy number differences between sensitive and resistant classes (P-value for rs2411377=0.04). The same group of markers also showed significant association between copy number and MMAE sensitivity (P-value for rs2411377=0.05). FIG. 2a shows the relationship between paclitaxel sensitivity and genomic DNA copy number in this part of chromosome 17. A significant number of cell lines (8 out of 14) that showed resistance to paclitaxel had an increase in gene amplification within the region (as indicated by a diamond). The heatmap generated by the analysis showed a genomic DNA copy number of least four in this region. None of the cell lines showing sensitivity to paclitaxel had a significant increase in genomic DNA copy number in this region. FIG. 2b shows similar data for MMAE sensitivity.

Example 5

Identification of Candidate Genes in the Interval

The chromosomal region from 17q21.31 to 17q21.33 encodes approximately 100 expressed transcripts according to the UC Santa Cruz Genome Browser (http://genome.ucsc.edu). Based on the principle that functionally relevant genes in regions of amplification should exhibit a concomitant increase in mRNA expression, this list was filtered down to 24 genes that showed significant overexpression upon amplification: ABCC3, COL1A1, CROP, EAP, EPN3, FLJ13855, FLJ20920, HOXB7, LOC201191, ITGB3, KIAA0924, KPNB1, LOC400604, LOC81558, MGC11242, MGC15396, NDP52, PDK2, PHB, PP1R9B, SLC35B1, SPOP, TOB1, WNT3. An example of significantly higher expression of the candidate gene ABCC3 (using Affymetrix expression probe set 208161_s_) in amplified cell lines compared to non-amplified cell lines is shown in FIG. 3. The 24 genes were subjected to functional analysis to identify the locus responsible for conferring resistance to taxanes and auristatins.

Example 6

Functional Validation of ABCC3 by RNA Interference

Figure 4A:
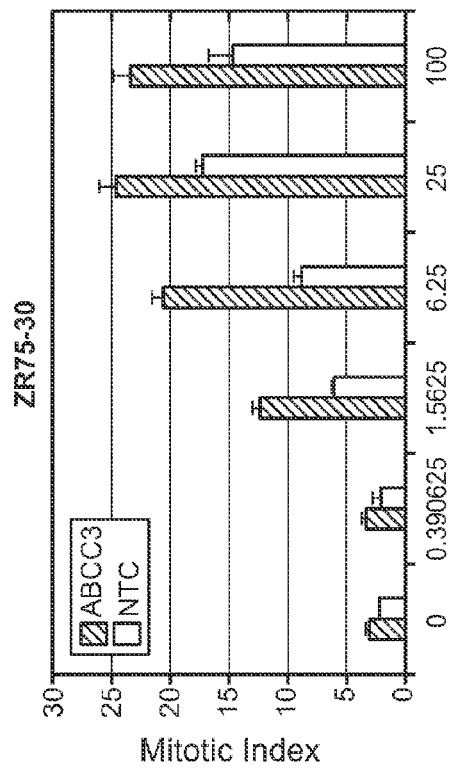
FIGS. 4a-4d show graphs representing mitotic index in response to paclitaxel treatment for four different cell lines after ABCC3 or control siRNA treatment. EFM-192A (a) and ZR-75-30 (b) cells have amplification and overexpression of ABCC3 and display enhanced sensitivity (increased mitotic index) after knockdown whereas HCC-1428 (c) and MDA-MB-453 (d) have low copy number and expression and do not show increased sensitivity.
Figure 4B:
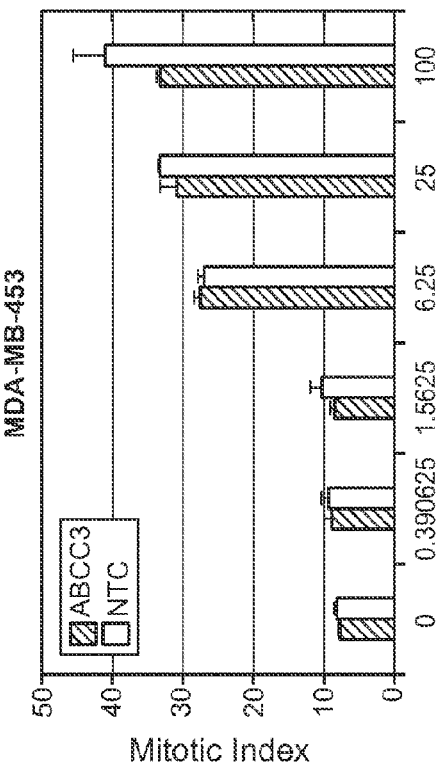
Figure 4C:
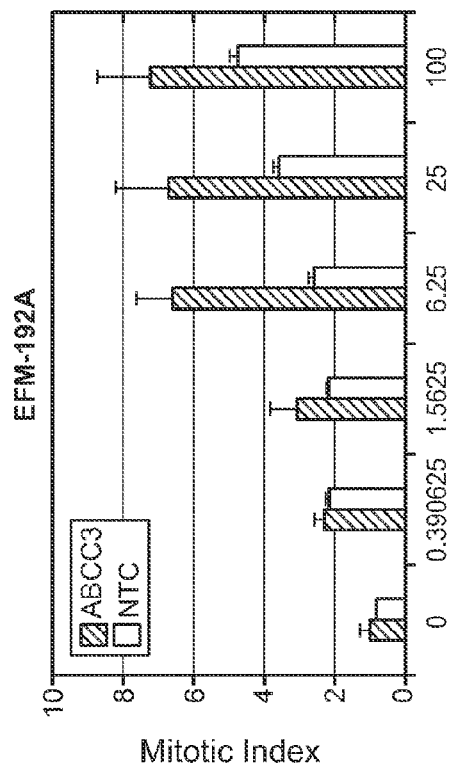
Figure 4D:
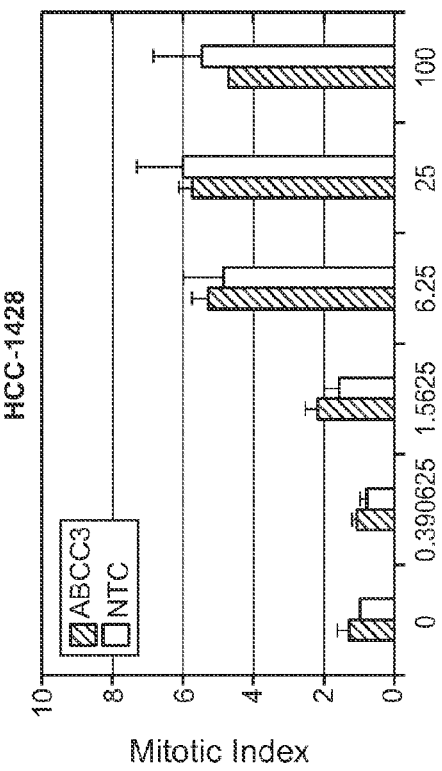

An RNA interference strategy was used to identify the gene responsible for mediating resistance to taxanes and auristatins in amplified cell lines. The assay employed made use of the fact that treatment of cells with paclitaxel or MMAE results in a block of cell cycle progression at M-phase that can be assayed by the presence of the mitotic marker phosphorylated histone H3 (33). Phosphorylation at Ser10 of histone H3 is tightly correlated with chromosome condensation during M phase, and the percentage of cells that are positive for pH3 staining, or mitotic index, can be determined through an immunofluorescence assay. Cellular knockdown of the gene mediating resistance should increase sensitivity of cell lines harboring the amplification to paclitaxel and MMAE and hence result in an accumulation of arrested cells and a higher mitotic index relative to control treated cells at a given drug concentration. Higher mitotic index correlates with reduction in viability and proliferation determined by other assays (COB and MRL, unpublished observations) but is a more specific readout of the antimitotic effects of these drugs. RNAi of 23 of the 24 candidate genes did not reproducibly result in accumulation of arrested cells and increased mitotic index in EFM-192A cells, but RNAi of ABCC3 resulted in a two to three fold increase in mitotic index relative to control treatment with a non-targeting control siRNA in the cell lines EFM-192A and ZR75-30 (FIG. 4a-b). In contrast, ABCC3 RNAi did not appreciably alter the mitotic index in non-amplified cell lines HCC-1428 and MDA-MB-453 (FIG. 4c-d). Similar results were obtained with MMAE.

Example 7

Overexpression of ABCC3 Causes In Vitro Multidrug Resistance

EVSA-T cells were selected as a model to generate ABCC3-overexpressing lines, since they do not show ABCC3 amplification and express low levels of ABCC3 transcripts. Three independently derived lines were confirmed to overexpress ABCC3 transcripts and screened for in vitro sensitivity to paclitaxel and MMAE using an ATP-based luminescence assay. In this experiment, treatment of ABCC3 overexpressing clones did not result in 50% reduction of cell viability in a three day assay so the fold-change in sensitivity was assessed by calculating the concentration that resulted in half-maximal response, or EC50. The EC50 for the vector control treated with paclitaxel was 0.2 nM while the EC50 values for the ABCC3-expressing lines were 5 nM, 10 nM, and 80 nM, respectively. The EC50 for the vector control treated with MMAE was 0.05 nM while the EC50 values for the ABCC3-expressing lines were 1.5 nM, 12 nM, and 90 nM, respectively.

All three overexpressing cell lines were at least 20-fold less sensitive to paclitaxel and MMAE based on EC50 values and also showed markedly less inhibition of cell growth compared to a vector-alone control stable cell line in an ATP-based luminescence assay (FIG. 5).

Example 8

Amplification of ABCC3 Occurs in Breast Tumors

Analysis of the region of chromosome 17 encompassing HER2 and ABCC3 in the cell line 100K SNP array data suggested that the ABCC3 amplicon was most commonly associated with the HER2 amplified subtypes and was not seen in the cell lines classified as luminal or basal-like.

To ensure that ABCC3 amplification was not a cell line specific phenomenon, copy number data at the ABCC3 locus was characterized using Agilent Array CGH (aCGH) arrays on DNA from 145 primary breast tumors. These tumor samples were also classified into luminal, basal-like, and HER2 subtypes using a predictor based on expression levels of ER, PR and HER2 as described in (32). ABCC3 copy number gains (>3.5 copies) are present in 25% of HER2 amplified and 11% of luminal tumors but were not present in basal-like tumors.

Example 9

FISH Assay

To confirm the cytogenetic basis of the apparent copy number gains observed by SNP and aCGH arrays, a fluorescence in situ hybridization (FISH) assay was developed using a BAC clone (see Example 1) spanning the ABCC3 locus and FISH analysis was performed on select cell lines and 61 primary tumors that had been classified as overexpressing HER2 based on the HerceptTest (IHC assay, reviewed in (35)). The FISH results from cell lines corroborated the data obtained from the SNP array and qPCR analyses. The breast cancer cell line EFM-192A predicted from SNP arrays to have elevated ABCC3 copy number did indeed exhibit a high level amplification of ABCC3 which is manifested as homogeneously staining regions (HSRs) with single or multiple integration into various chromosomes while maintaining single copies of HER2 and ABCC3 on chromosome 17. Cell lines predicted to be diploid for ABCC3 based on SNP array analysis were confirmed to be diploid based on FISH analysis with CEP17 and ABCC3. FISH analysis of the 61 HER2 positive primary tumors that were screened for ABCC3 amplification confirmed that elevated copy number at ABCC3 is common in HER2 positive breast tumors. High level gene amplification (>2.2 ratio of ABCC3/CEP17) was seen in 25% of the tumors, while an additional 11% of the tumors showed moderate increases for ABCC3 (3-7 copies of ABCC3). Interestingly, a number of tumors show evidence of heterogeneity and exhibit cells with both very high level amplification of ABCC3 alongside cells with diploid copy number of ABCC3.

Example 10

Overexpression of ABCC3 Causes Resistance to DM1

Figure 7:
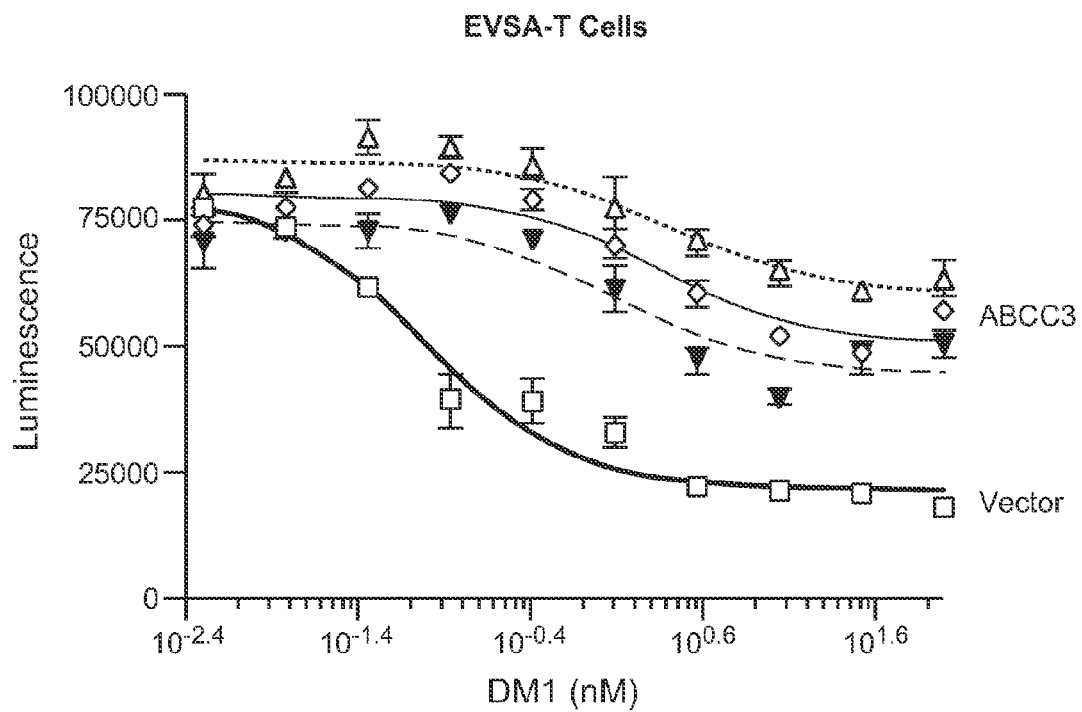
FIG. 7 shows three ABCC3 overexpressing clones and a control cell line analyzed for sensitivity to free DM1 in a standard cell viability assay.

EVSA-T cells were stably transfected with an ABCC3 containing plasmid where ABCC3 is expressed at high levels from a cytomegalovirus (CMV) promoter. Overexpression of ABCC3 was confirmed by qRT-PCR. Three overexpressing clones and a control cell line were then analyzed for sensitivity to free DM1 in a standard cell viability assay and it was found that the overexpressing clones were more resistant to DM1 than the control cell line, consistent with ABCC3 overexpression leading to resistance to this agent (FIG. 7).

Example 11

ABCC3 RNAi Enhances Response to MMAF Antibody Conjugate

Figure 8:
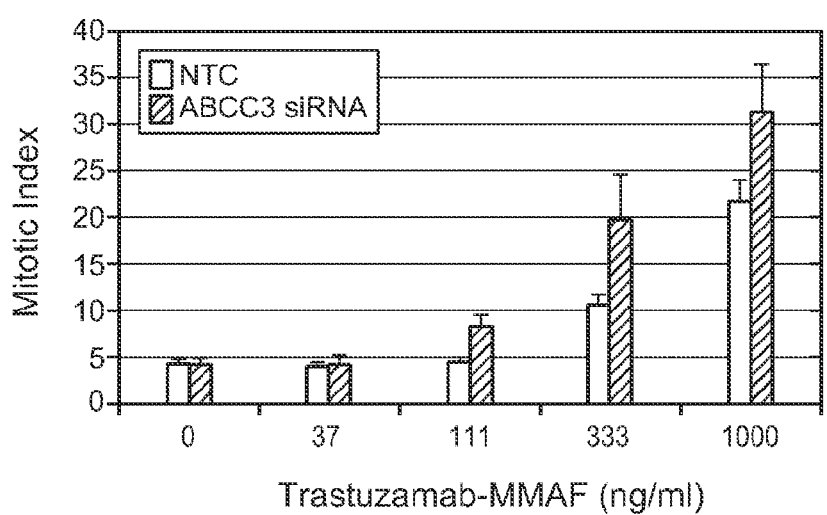
FIG. 8 shows a graph representing mitotic index EFM-192A cells transfected with control (NTC) or ABCC3 siRNA when treated with trastuzamab-mc-vc-PAB-MMAF.

EFM192A cells were transfected with ABCC3 siRNA and were subjected to treatment with trastuzamab (Herceptin) conjugated via the drug linker reagent maleimidocaproyl-valine-citrulline-PAB to MMAF (trastuzamab-mc-vc-PAB-MMAF). The EFM-192A cells transfected with ABCC3 siRNA are more sensitive to trastuzamab-mc-vc-PAB-MMAF than cells transfected with a control siRNA indicating that ABCC3 expression levels can impact sensitivity to this agent (FIG. 8).

Example 12

ABCC3 RNAi Enhances Response to Free DM1 and Trastuzumab-smcc-DM1 Conjugate

Figure 9A:
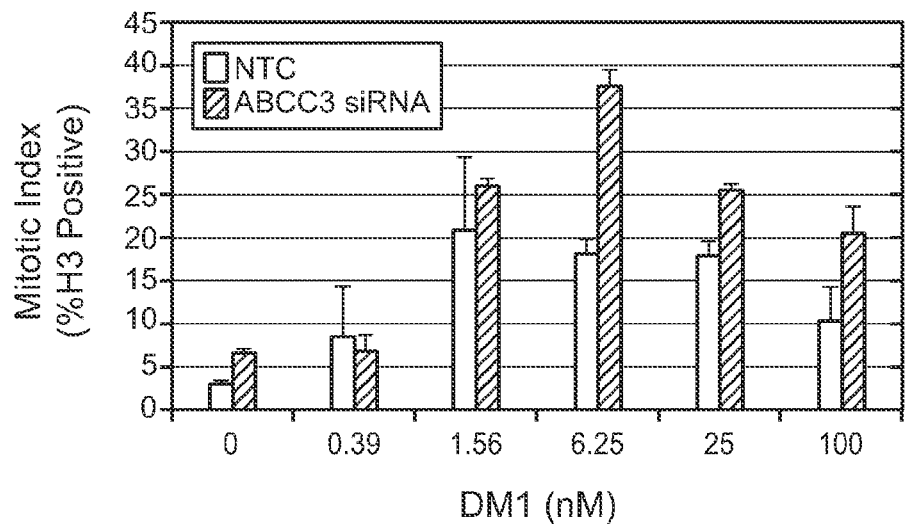
FIG. 9a shows the mitotic response of EFM-192A cells transfected with control (NTC) or ABCC3 siRNA when treated with free DM1.
Figure 9B:
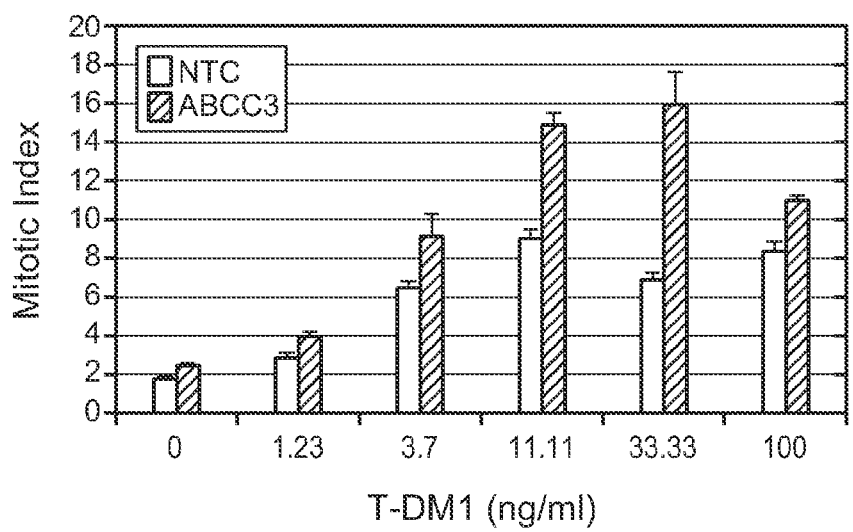
FIG. 9b shows the mitotic response of EFM-192A cells transfected with control (NTC) or ABCC3 siRNA when treated with T-DM1.

EFM-192A cells transfected with ABCC3 siRNA are more sensitive to either free DM1 or Trastuzumab-smcc-DM1 conjugate than cells transfected with a control siRNA (NTC), indicating that ABCC3 expression levels can impact sensitivity to these agents (FIGS. 9a and 9b).

Example 13

ABCC3 Amplification Status Correlates with T-DM1 Activity

ABCC3 FISH analysis was performed on samples obtained from the T-DM1 Phase II (TDM4258G) trial to explore the effect of ABCC3 amplification on T-DM1 activity in HER2 amplified breast tumors. The TDM4258G trial is a multi-institutional, open-label, single-arm, Phase II study of T-DM1 administered by IV infusion to patients with HER2-positive metastatic breast cancer. The patients in the trial had shown prior progression on HER2-directed therapy. Formalin Fixed Paraffin Embedded (FFPE) archival tumor tissue samples from the clinical trial was obtained from the clinical investigation sites with appropriate IRB approval and patient consent.

The FISH assay was performed on the clinical trial samples as described in Example 1. FIG. 10 shows the data from the analysis of the FISH assay sorted by ratio of ABCC3/CEP17. Those samples with ABCC3/CEP17 ratios of 1.8 and above are considered to have ABCC3 amplification. 80% (12/15) of patients whose samples showed no amplification of ABCC3 responded to treatment to T-DM1 while 40% (2/5) of patients whose samples showed amplification of ABCC3 responded to T-DM1 treatment. This analysis indicates that ABCC3 amplification status is useful in determining the likely response of a patient to treatment with T-DM1.

REFERENCES

1. O'Driscoll L, Clynes M. Biomarkers and multiple drug resistance in breast cancer. Curr Cancer Drug Targets 2006; 6(5):365-84.
2. Cigler T, Goss P E. Breast cancer adjuvant endocrine therapy. Cancer journal (Sudbury, Mass. 2007; 13(3):148-55.
3. Slamon D J, Leyland-Jones B, Shak S, et al. Use of chemotherapy plus a monoclonal antibody against HER2 for metastatic breast cancer that overexpresses HER2. N Engl J Med 2001; 344(11):783-92.
4. Guarneri V, Conte P F. The curability of breast cancer and the treatment of advanced disease. Eur J Nucl Med Mol Imaging 2004; 31 Suppl 1:S149-61.
5. Szakacs G, Paterson J K, Ludwig J A, Booth-Genthe C, Gottesman M M. Targeting multidrug resistance in cancer. Nature reviews 2006; 5(3):219-34.
6. Katsnelson A. Cautious welcome for FDA pharmacogenomics guidance. Nat Biotechnol 2005; 23(5):510.
7. Lee J K, Havaleshko D M, Cho H, et al. A strategy for predicting the chemosensitivity of human cancers and its application to drug discovery. Proc Natl Acad Sci USA 2007; 104(32):13086-91.
8. Szakacs G, Annereau J P, Lababidi S, et al. Predicting drug sensitivity and resistance: profiling ABC transporter genes in cancer cells. Cancer Cell 2004; 6(2):129-37.
9. Sorlie T, Tibshirani R, Parker J, et al. Repeated observation of breast tumor subtypes in independent gene expression data sets. Proc Natl Acad Sci USA 2003; 100(14):8418-23.
10. Finnegan T J, Carey L A. Gene-expression analysis and the basal-like breast cancer subtype. Future Oncol 2007; 3(1):55-63.
11. Hu Z, Fan C, Oh D S, et al. The molecular portraits of breast tumors are conserved across microarray platforms. BMC Genomics 2006; 7:96.
12. Kurt M, Harputluoglu H, Dede D S, Gullu I H, Altundag K. Potential molecular targeted therapies in the management of the basal-like subtype of breast cancer. Breast 2007; 16(2):111-2.
13. Rouzier R, Perou C M, Symmans W F, et al. Breast cancer molecular subtypes respond differently to preoperative chemotherapy. Clin Cancer Res 2005; 11(16):5678-85.
14. Neve R M, Chin K, Fridlyand J, et al. A collection of breast cancer cell lines for the study of functionally distinct cancer subtypes. Cancer Cell 2006; 10(6):515-27.
15. Doronina S O, Toki B E, Torgov M Y, et al. Development of potent monoclonal antibody auristatin conjugates for cancer therapy. Nat Biotechnol 2003; 21(7):778-84.
16. Crown J, O'Leary M. The taxanes: an update. Lancet 2000; 355(9210):1176-8.
17. Zhao X, Li C, Paez J G, et al. An integrated view of copy number and allelic alterations in the cancer genome using single nucleotide polymorphism arrays. Cancer Res 2004; 64(9):3060-71.
18. Garraway L A, Widlund H R, Rubin M A, et al. Integrative genomic analyses identify MITF as a lineage survival oncogene amplified in malignant melanoma. Nature 2005; 436(7047):117-22.
19. Gorringe K L, Chin S F, Pharoah P, et al. Evidence that both genetic instability and selection contribute to the accumulation of chromosome alterations in cancer. Carcinogenesis 2005; 26(5):923-30.
20. Rae J M, Ramus S J, Waltham M, et al. Common origins of MDA-MB-435 cells from various sources with those shown to have melanoma properties. Clin Exp Metastasis 2004; 21(6):543-52.
21. Barrett M T, Scheffer A, Ben-Dor A, et al. Comparative genomic hybridization using oligonucleotide microarrays and total genomic DNA. Proc Natl Acad Sci USA 2004; 101(51):17765-70.
22. Eisen M B, Spellman P T, Brown P O, Botstein D. Cluster analysis and display of genome-wide expression patterns. Proc Natl Acad Sci USA 1998; 95(25):14863-8.
23. Matsuzaki H, Dong S, Loi H, et al. Genotyping over 100,000 SNPs on a pair of oligonucleotide arrays. Nat Methods 2004; 1(2):109-11.
24. Hupe P, Stransky N, Thiery J P, Radvanyi F, Barillot E. Analysis of array CGH data: from signal ratio to gain and loss of DNA regions. Bioinformatics 2004; 20(18):3413-22.
25. Beroukhim R, Getz G, Nghiemphu L, et al. Assessing the significance of chromosomal aberrations in cancer: Methodology and application to glioma. Proc Natl Acad Sci USA 2007; 104(50):20007-12.
26. Westphal P, Young S. Resampling-based multiple testing: Examples and methods for p-value adjustment.: John Wiley & Sons 1993.
27. Fanning T G, Singer M F. LINE-1: a mammalian transposable element. Biochimica et biophysica acta 1987; 910(3):203-12.
28. Kindich R, Florl A R, Jung V, et al. Application of a modified real-time PCR technique for relative gene copy number quantification to the determination of the relationship between NKX3.1 loss and MYC gain in prostate cancer. Clin Chem 2005; 51(3):649-52.
29. Bayani J, Zielenska M, Marrano P, et al. Molecular cytogenetic analysis of medulloblastomas and supratentorial primitive neuroectodermal tumors by using conventional banding, comparative genomic hybridization, and spectral karyotyping. J Neurosurg 2000; 93(3):437-48.
30. Grove L E, Ghosh R N. Quantitative characterization of mitosis-blocked tetraploid cells using high content analysis. Assay and drug development technologies 2006; 4(4): 421-42.
31. Livasy C A, Karaca G, Nanda R, et al. Phenotypic evaluation of the basal-like subtype of invasive breast carcinoma. Mod Pathol 2006; 19(2):264-71.
32. Hu X S H, O'Brien C, Honchell, Wu T, Chant J, Lackner M, Cavet G. Genetic alterations and oncogenic pathways associated with breast cancer subtypes. Molecular Cancer Research, in press (April, 2009).
33. Gasparri F, Cappella P, Galvani A. Multiparametric cell cycle analysis by automated microscopy. J Biomol Screen 2006; 11(6):586-98.
34. Borst P, Evers R, Kool M, Wijnholds J. A family of drug transporters: the multidrug resistance-associated proteins. J Natl Cancer Inst 2000; 92(16):1295-302.
35. Carlsson J, Nordgren H, Sjostrom J, et al. HER2 expression in breast cancer primary tumours and corresponding metastases. Original data and literature review. Br J Cancer 2004; 90(12):2344-8.

36. Liu Y, Peng H, Zhang J T. Expression profiling of ABC transporters in a drug-resistant breast cancer cell line using AmpArray. Mol Pharmacol 2005; 68(2):430-8.

37. Huang R, Murry D J, Kolwankar D, Hall S D, Foster D R. Vincristine transcriptional regulation of efflux drug transporters in carcinoma cell lines. Biochem Pharmacol 2006; 71(12):1695-704.

38. Huisman M T, Chhatta A A, van Tellingen O, Beijnen J H, Schinkel A H. MRP2 (ABCC2) transports taxanes and confers paclitaxel resistance and both processes are stimulated by probenecid. Int J Cancer 2005; 116(5):824-9.

39. Hopper-Borge E, Chen Z S, Shchaveleva I, Belinsky M G, Kruh G D. Analysis of the drug resistance profile of multidrug resistance protein 7 (ABCC10): resistance to docetaxel. Cancer Res 2004; 64(14):4927-30.

40. Lagas J S, Vlaming M L, van Tellingen O, et al. Multidrug resistance protein 2 is an important determinant of paclitaxel pharmacokinetics. Clin Cancer Res 2006; 12(20 Pt 1):6125-32.

41. Kool M, van der Linden M, de Haas M, et al. MRP3, an organic anion transporter able to transport anti-cancer drugs. Proc Natl Acad Sci USA 1999; 96(12):6914-9.

42. Zeng H, Bain L J, Belinsky M G, Kruh G D. Expression of multidrug resistance protein-3 (multispecific organic anion transporter-D) in human embryonic kidney 293 cells confers resistance to anticancer agents. Cancer Res 1999; 59(23):5964-7.

43. Mahjoubi F, Hill R J, Peters G B. Chromosome microdissection identifies genomic amplifications associated with drug resistance in a leukemia cell line: an approach to understanding drug resistance in cancer. Chromosome Res 2006; 14(3):263-76.

44. Schmidt M, Bremer E, Hasenclever D, et al. Role of the progesterone receptor for paclitaxel resistance in primary breast cancer. Br J Cancer 2007; 96(2):241-7.

45. Shajahan A N, Wang A, Decker M, Minshall R D, Liu M C, Clarke R. Caveolin-1 tyrosine phosphorylation enhances paclitaxel-mediated cytotoxicity. J Biol Chem 2006.

46. Pinilla S M, Honrado E, Hardisson D, Benitez J, Palacios J. Caveolin-1 expression is associated with a basal-like phenotype in sporadic and hereditary breast cancer. Breast Cancer Res Treat 2006; 99(1):85-90.

47. Savage K, Lambros M B, Robertson D, et al. Caveolin 1 is overexpressed and amplified in a subset of basal-like and metaplastic breast carcinomas: a morphologic, ultrastructural, immunohistochemical, and in situ hybridization analysis. Clin Cancer Res 2007; 13(1):90-101.

48. Rouzier R, Rajan R, Wagner P, et al. Microtubule-associated protein tau: a marker of paclitaxel sensitivity in breast cancer. Proc Natl Acad Sci USA 2005; 102(23):8315-20.

49. Wagner P, Wang B, Clark E, Lee H, Rouzier R, Pusztai L. Microtubule Associated Protein (MAP)-Tau: a novel mediator of paclitaxel sensitivity in vitro and in vivo. Cell Cycle 2005; 4(9):1149-52.

50. Lambros M B, Natrajan R, Reis-Filho J S. Chromogenic and fluorescent in situ hybridization in breast cancer. Hum Pathol 2007; 38(8):1105-22.

51. Hann C L, Brahmer J R. "Who should receive epidermal growth factor receptor inhibitors for non-small cell lung cancer and when?" Curr Treat Options Oncol 2007; 8(1):28-37.

52. Hayes D F, Thor A D, Dressler L G, et al. HER2 and response to paclitaxel in node-positive breast cancer. N Engl J Med 2007; 357(15):1496-506.

Although the invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

What is claimed is:

1. A method of treating breast cancer, comprising (a) determining, in a tissue sample obtained from a human patient with HER2-positive breast cancer who had shown prior progression on HER2-directed therapy, a copy number of an ABCC3 (ATP-Binding Cassette, Sub-Family C, Member 3) gene or an ABCC3 gene amplification value, relative to an amplification value of a centromere 17 (CEP17) gene in the same tissue sample, by fluorescence in situ hybridization (FISH), and (b) administering to the patient whose breast cancer is characterized by an ABCC3 gene copy number of less than 3 or an ABCC3 gene amplification value of less than 1.8 relative to an amplification value of a CEP17 gene an effective amount of a conjugate of trastuzumab and N2'-deacetyl-N2'-(3-mercapto-1-oxopropyl)maytansine (DM1), or a conjugate of trastuzumab and monomethyl auristatin E (MMAE).

2. The method of claim 1, wherein said conjugate is trastuzumab-N-succinimidyl-4-(N-maleimidomethyl) cyclohexane-1-carboxylate (MCC)-DM1 (T-DM1).

* * * * *